United States Patent
Hou et al.

(10) Patent No.: US 12,174,205 B2
(45) Date of Patent: Dec. 24, 2024

(54) PHOSPHATIDYLETHANOLAMINE-SPECIFIC PROBES

(71) Applicant: Northwestern University, Evanston, IL (US)

(72) Inventors: Songwang Hou, Brookfield, WI (US); Ming Zhao, Oak Park, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/304,671

(22) PCT Filed: Apr. 17, 2015

(86) PCT No.: PCT/US2015/026416
§ 371 (c)(1),
(2) Date: Oct. 17, 2016

(87) PCT Pub. No.: WO2016/167798
PCT Pub. Date: Oct. 20, 2016

(65) Prior Publication Data
US 2018/0031583 A1     Feb. 1, 2018

Related U.S. Application Data

(60) Provisional application No. 61/981,029, filed on Apr. 17, 2014.

(51) Int. Cl.
| | | |
|---|---|---|
| *G01N 33/92* | (2006.01) | |
| *A61K 38/12* | (2006.01) | |
| *A61K 49/00* | (2006.01) | |
| *C08G 65/334* | (2006.01) | |
| *C09K 11/07* | (2006.01) | |
| *G01N 33/58* | (2006.01) | |

(52) U.S. Cl.
CPC ............. *G01N 33/92* (2013.01); *A61K 38/12* (2013.01); *A61K 49/0047* (2013.01); *A61K 49/0056* (2013.01); *C08G 65/3348* (2013.01); *C09K 11/07* (2013.01); *G01N 33/582* (2013.01); *C09K 2211/14* (2013.01); *G01N 2405/04* (2013.01)

(58) Field of Classification Search
None
See application file for complete search history.

(56) References Cited

U.S. PATENT DOCUMENTS

| | | |
|---|---|---|
| 6,406,693 B1 | 6/2002 | Thorpe et al. |
| 2004/0170620 A1* | 9/2004 | Thorpe ................. A61K 39/395 424/130.1 |
| 2010/0136614 A1 | 6/2010 | Luo et al. |
| 2012/0202217 A1 | 8/2012 | Adamczyk et al. |

FOREIGN PATENT DOCUMENTS

| | | |
|---|---|---|
| WO | WO 2010/126551 | 11/2010 |
| WO | WO 2016/167798 | 10/2016 |

OTHER PUBLICATIONS

Sano et al. ("Short PEG-linkers improve the performance of targeted, activatable monoclonal antibody-Indocyanine green optical imaging probes"; Bioconjug Chem May 2013: 24(5):811-816).*
Snapp ("Design and Use of Fluorescent Fusion Proteins in Cell Biology" Curr Protoc Cell Biol. 2010).*
Trabulo et al. (Cell-Penetrating Peptides—Mechanisms of Cellular uptake and Generation of Delivery Systems; Pharmaceuticals Review; Mar. 2010).*
Invitrogen ("Vivid Colors pcDNA 6.2/EmGFP and YFP-GW/TOPT mammalial expression vectors" Dec. 14, 2010).*
Stafford et al. ("Increased Exposure of Phosphatidylethanolamine on the surface of tumor vascular endothelium" NeoPlasia; vol. 13 (4) Apr. 2011).*
Toseland et al. ("Fluorescent labeling and modification of proteins"; J. Chem Biol. (2013)6:85-95).*
Allen et al. Membrane contact, fusion, and hexagonal (HII) transitions in phosphatidylethanolamine liposomes. Biochemistry. Mar. 27, 1990;29(12):2976-85.
Aoki et al. A novel peptide probe for studying the transbilayer movement of phosphatidylethanolamine. J Biochem. Aug. 1994;116(2):291-7.
Bogdanov et al. Lipids and topological rules governing membrane protein assembly. Biochim Biophys Acta. Aug. 2014;1843(8):1475-88.
Bogdanov et al. Phospholipid-assisted refolding of an integral membrane protein. Minimum structural features for phosphatidylethanolamine to act as a molecular chaperone. J Biol Chem. Apr. 30, 1999;274(18):12339-45.
Chen et al. Endocytic sorting and recycling require membrane phosphatidylserine asymmetry maintained by TAT-1/CHAT-1. PLoS Genet. Dec. 9, 2010;6(12):e1001235.
Cinelli et al. The enhanced green fluorescent protein as a tool for the analysis of protein dynamics and localization: local fluorescence study at the single-molecule level. Photochem Photobiol. Jun. 2000;71(6):771-6.
Das et al. Flippase-mediated phospholipid asymmetry promotes fast Cdc42 recycling in dynamic maintenance of cell polarity. Nat Cell Biol. Feb. 19, 2012;14(3):304-10.

(Continued)

*Primary Examiner* — James H Alstrum-Acevedo
*Assistant Examiner* — Tara L Martinez
(74) *Attorney, Agent, or Firm* — Benesch Friedlander Coplan & Aronoff LLP

(57) ABSTRACT

Provided herein are phosphatidylethanolamine (PE)-specific probes and methods of use thereof. In particular, the present invention provides conjugates of PE binding moieties with detectable markers, and methods of use thereof to detect and/or characterize PE within cells.

2 Claims, 14 Drawing Sheets

Specification includes a Sequence Listing.

(56) References Cited

OTHER PUBLICATIONS

Emoto et al. Exposure of phosphatidylethanolamine on the surface of apoptotic cells. Exp Cell Res. May 1, 1997;232(2):430-4.

Fairn et al. High-resolution mapping reveals topologically distinct cellular pools of phosphatidylserine. J Cell Biol. Jul. 25, 2011;194(2):257-75.

Gadella and Harrison. Capacitation induces cyclic adenosine 3',5'-monophosphate-dependent, but apoptosis-unrelated, exposure of aminophospholipids at the apical head plasma membrane of boar sperm cells. Biol Reprod. Jul. 2002;67(1):340-50.

Hanada et al. The amino-terminal region of Atg3 is essential for association with phosphatidylethanolamine in Atg8 lipidation. FEBS Lett. Apr. 2, 2009;583(7):1078-83.

Hou et al. Membrane phospholipid redistribution in cancer microparticles and implications in the recruitment of cationic protein factors. J Extracell Vesicles. Jun. 11, 2014;3, 10 pages.

Jean and Kiger. Coordination between RAB GTPase and phosphoinositide regulation and functions. Nat Rev Mol Cell Biol. Jun. 22, 2012;13(7):463-70.

Kay and Grinstein. Phosphatidylserine-mediated cellular signaling. Adv Exp Med Biol. 2013;991:177-93.

Kutateladze. Translation of the phosphoinositide code by PI effectors. Nat Chem Biol. Jul. 2010;6(7):507-13.

Kylmchenko et al. Fluorescent probes for lipid rafts: from model membranes to living cells. Chem Biol. Jan. 16, 2014;21(1):97-113.

Machaidze and Seelig. Specific binding of cinnamycin (Ro 09-0198) to phosphatidylethanolamine. Comparison between micellar and membrane environments. Biochemistry. Nov. 4, 2003;42(43):12570-6.

Machaidze et al. Specific binding of Ro 09-0198 (cinnamycin) to phosphatidylethanolamine: a thermodynamic analysis. Biochemistry. Feb. 12, 2002;41(6):1965-71.

Maiuri et al. Self-eating and self-killing: crosstalk between autophagy and apoptosis. Nat Rev Mol Cell Biol. Sep. 2007;8(9):741-52.

Makino et al. Cinnamycin (Ro 09-0198) promotes cell binding and toxicity by inducing transbilayer lipid movement. J Biol Chem. Jan. 31, 2003;278(5):3204-9.

Martin et al. Early redistribution of plasma membrane phosphatidylserine is a general feature of apoptosis regardless of the initiating stimulus: inhibition by overexpression of Bcl-2 and Abl. J Exp Med. Nov. 1, 1995;182(5):1545-56.

Menon and Stevens. Phosphatidylethanolamine is the donor of the ethanolamine residue linking a glycosylphosphatidylinositol anchor to protein. J Biol Chem. Aug. 5, 1992;267(22):15277-80.

Muralidharan-Chari et al. Microvesicles: mediators of extracellular communication during cancer progression. J Cell Sci. May 15, 2010;123(Pt 10):1603-11.

Navarro et al. Interaction of duramycin with artificial and natural membranes. Biochemistry. Aug. 13, 1985;24(17):4645-50.

Oh-Oka et al. Physiological pH and acidic phospholipids contribute to substrate specificity in lipidation of Atg8. J Biol Chem. Aug. 8, 2008;283(32):21847-52.

Sayner et al. Filamin A is a phosphorylation target of membrane but not cytosolic adenylyl cyclase activity. Am J Physiol Lung Cell Mol Physiol. Jul. 2011;301(1):L117-24.

Sebastian et al. Phospholipid flippases: building asymmetric membranes and transport vesicles. Biochim Biophys Acta. Aug. 2012;1821(8):1068-77.

Shiratsuchi et al. Essential role of phosphatidylserine externalization in apoptosing cell phagocytosis by macrophages. Biochem Biophys Res Commun. May 19, 1998;246(2):549-55.

Siegel and Epand. Effect of influenza hemagglutinin fusion peptide on lamellar/inverted phase transitions in dipalmitoleoylphosphatidylethanolamine: implications for membrane fusion mechanisms. Biochim Biophys Acta. Sep. 29, 2000;1468(1-2):87-98.

Tatsuta et al. Mitochondrial lipid trafficking. Trends Cell Biol. Jan. 2014;24(1):44-52.

Van Meer et al. Membrane lipids: where they are and how they behave. Nat Rev Mol Cell Biol. Feb. 2008;9(2):112-24.

Vance and Tasseva. Formation and function of phosphatidylserine and phosphatidylethanolamine in mammalian cells. Biochim Biophys Acta. Mar. 2013;1831(3):543-54.

Wang et al. Early hypercytokinemia is associated with interferon-induced transmembrane protein-3 dysfunction and predictive of fatal H7N9 infection. Proc Natl Acad Sci U S A. Jan. 14, 2014;111(2):769-74.

Wehman et al. The P4-ATPase TAT-5 inhibits the budding of extracellular vesicles in C. elegans embryos. Curr Biol. Dec. 6, 2011;21(23):1951-9.

Yang and Ding. New phases of phospholipids and implications to the membrane fusion problem. Biochemistry. Jun. 10, 2003;42(22):6631-5.

Yeung et al. Membrane phosphatidylserine regulates surface charge and protein localization. Science. Jan. 11, 2008;319(5860):210-3.

Zhao et al. 99mTc-labeled duramycin as a novel phosphatidylethanolamine-binding molecular probe. J Nucl Med. Aug. 2008;49(8):1345-52.

Zhao. Lantibiotics as probes for phosphatidylethanolamine. Amino Acids. Nov. 2011;41(5):1071-9.

International Search Report and Written Opinion for PCT/US2015. 026416 mailed Jul. 24, 2015, 11 pages.

\* cited by examiner

ER signal intensity match

PHOSPHATIDYLETHANOLAMINE-SPECIFIC PROBES

CROSS REFERENCE TO RELATED APPLICATIONS

The present invention claims the priority to U.S. Provisional Patent Application No. 61/981,029, filed Apr. 17, 2014, which is incorporated by reference in its entirety.

STATEMENT REGARDING FEDERAL SUPPORT

This invention was made with government support under 1 R01 HL102085 awarded by the National Institutes of Health. The government has certain rights in the invention

FIELD

Provided herein are phosphatidylethanolamine (PE)-specific probes and methods of use thereof In particular, the present invention provides conjugates of PE binding moieties with detectable markers, and methods of use thereof to detect and/or characterize PE within cells.

BACKGROUND

By nature of their structural features, various phospholipids in cellular membranes contribute to distinct biological roles (van Meer et al. *Nat Rev Mol Cell Biol.* 9, 112-224 (2008); Kutateladze. *Nat Chem Biol.* 6, 507-513 (2010); Jean & Kiger. *Nat Rev Mol Cell Biol.* 13, 463-470 (2012); Kay & Grinstein. *Adv Exp Med Biol.* 991, 177-193 (2013); Yeung et al. *Science.* 319, 210-213 (2008); herein incorporated by reference in their entireties). These processes are mediated by the differential distribution of phospholipids among cellular compartments. The stereospecific and electrostatic signaling mechanisms involving phosphatidylinositides (PIs) have been extensively documented. Growing evidence has substantiated the roles of phosphatidylserine (PS) in maintaining an electrostatic gradient that regulates protein-membrane interactions.

Phosphatidylethanolamine (PE) is a zwitterionic aminophospholipid at physiological pH, with a relatively small ethanolamine head group. It is the second most abundant phospholipid in mammalian cells. The biosynthesis of PE takes place predominantly at the ER and the inner membrane of mitochondria (Vance & Tasseva. Biochim Biophys Acta. 1831, 543-554 (2013); herein incorporated by reference in its entirety). Once synthesized, PE participates extensively in cellular membrane trafficking, and as a precursor in synthetic pathways for other phospholipids and bioconjugates. The physicochemical properties of PE are implicative of a distinct set of utilities. Despite its ubiquitous presence, however, the biological roles of PE in mammalian cellular membrane systems remain to be fully defined.

Current knowledge on the intracellular distribution of PE has been derived mainly from cell fractionation and biochemical studies. While these measurements provide a global estimate of PE content, a spatially-defined characterization in intact, live cells will add vital, complementary information. Phosphatidylethanolamine (PE) is a ubiquitous phospholipid and a major component in cellular membranes. Very little is known about the topological distribution of PE in intracellular membrane networks.

SUMMARY

Provided herein are phosphatidylethanolamine (PE)-specific probes and methods of use thereof In particular, the present invention provides conjugates of PE binding moieties with detectable markers, and methods of use thereof to detect and/or characterize PE within cells.

In some embodiments, the present invention provides compositions comprising a conjugate of a phosphatidylethanolamine-binding moiety and a detectable moiety. In some embodiments, the PE-binding moiety has at least 50% sequence identity (e.g., >60%, >70%, >80%, >90%, >95%) with duramycin and is capable of stably binding phosphatidylethanolamine (PE). In some embodiments, the PE-binding moiety has at least 70% sequence similarity (e.g., >80%, >90%, >95%) with duramycin and is capable of stably binding phosphatidylethanolamine (PE). In some embodiments, the PE-binding moiety is duramycin. In some embodiments, the detectable moiety is selected from the list consisting of: a radiolabel, a hapten, a binding moiety, a fluorescent moiety, a chromophore, a mass tag, a contrast agent, a spin label, a handle, and a surface. In some embodiments, the detectable moiety comprises a fluorescent moiety. In some embodiments, the detectable moiety comprises a fluorescent protein. In some embodiments, the detectable moiety comprises a polypeptide having 50% sequence identity (e.g., >60%, >70%, >80%, >90%, >95%) with enhanced green fluorescent protein (e.g., full length EGFP). In some embodiments, the detectable moiety comprises a polypeptide having 70% sequence similarity (e.g., >80%, >90%, >95%) with enhanced green fluorescent protein (e.g., full length EGFP). In some embodiments, the detectable moiety comprises enhanced green fluorescent protein (EGFP). In some embodiments, the detectable moiety and the PE-binding agent are connected by a linker moiety. In some embodiments, the linker moiety is a PEG linker or a peptide linker. In some embodiments, the conjugate further comprises a functional moiety. In some embodiments, the functional moiety is a localization signal. In some embodiments, the localization signal is Tat peptide. In some embodiments, the conjugate is nontoxic to cells. In some embodiments, the conjugate is cell permeable.

In some embodiments, the present invention comprises a conjugate of: (a) duramycin; and (b) enhanced green fluorescent protein, or derivatives or analogues thereof In some embodiments, the conjugate further comprises Tat peptide. In some embodiments, the duramycin and enhanced green fluorescent protein are conjugated by a PEG linker.

In some embodiments, the present invention provides methods of detecting PE in a cell comprising: (a) exposing the cell to a conjugate of a PE-binding agent and a detectable moiety; and (b) detecting said detectable moiety.

In some embodiments, the present invention provides methods of locating PE in a cell comprising: (a) exposing the cell to a conjugate of a PE-binding agent and a detectable moiety; and (b) detecting the location of said detectable moiety in said cell.

In some embodiments, the present invention provides methods of identifying a cellular entity that colocalizes with PE, comprising (a) exposing the cell to a conjugate of a PE-binding agent and a detectable moiety; (b) labeling said cellular entity with a second detectable label; and (c) detecting said detectable label and said second detectable label to determine the cellular location of said PE and said cellular entity. In some embodiments, detecting said detectable label and said second detectable label comprises detecting energy transfer from said detectable label to said second detectable label or from said second detectable label to said detectable label.

In some embodiments, the present invention provides methods of monitoring the effect of cellular events on PE within a cell, comprising: (a) contacting a cell with a conjugate of a PE-binding agent and a detectable moiety; (b) detecting said detectable moiety before said cellular event; (c) inducing a cellular event; and (d) detecting said detectable moiety after said cellular event. In some embodiments, said detectable moiety is monitored in real-time during said cellular event.

In some embodiments, the present invention provides methods of monitoring the effect of a stimulus on PE within a cell, comprising: (a) contacting a cell with a conjugate of a PE-binding agent and a detectable moiety; (b) detecting said detectable moiety before said stimulus; (c) exposing said cell to said stimulus; and (d) detecting said detectable moiety after said stimulus. In some embodiments, said detectable moiety is monitored in real-time during exposure to said stimulus. In some embodiments, a stimulus is a toxin, therapeutic, cell component, condition (e.g., temperature, pH, salt concentration, etc.), peptide, lipid, etc.

In some embodiments, the present invention provides methods of monitoring cellular membranes (e.g., plasma membrane, nuclear membrane, golgi, endoplasmic resticulum, other organellar membranes, etc.) comprising: (a) contacting a cell with a conjugate of a PE-binding agent and a detectable moiety; (b) allowing said PE-binding moiety to interact with PE; (c) detecting said detectable moiety. In some embodiments, said detectable moiety is monitored in real-time to monitor changes to said cellular membrane (e.g., during the cell cycle, in response to stimuli, in response to cellular events of pathways, etc.).

In some embodiments, a conjugate of a PE-binding agent and a detectable moiety is administered to cells (e.g., extracellularly). In some embodiments, a conjugate of a PE-binding agent and a detectable moiety is cell permeable and enters the cell. In other embodiments, a cell is permeablized to allow entry of a PE-binding agent and a detectable moiety. In some embodiments, a conjugate of a PE-binding agent and a detectable moiety is expressed within a cell.

In some embodiments, a conjugate of a PE-binding agent and a detectable moiety is used to detect, locate, and/or characterize PE extracellularly, in situ, in non-cellular environment, in cell lysate, in vitro, etc.

In some embodiments, kits and/or reaction mixtures comprising a conjugate of a PE-binding agent and a detectable moiety are provided. In some embodiments, kits and/or reaction mixtures further comprise buffers, assay reagents, cells, other probes, etc.

DEFINITIONS

Figure 1:
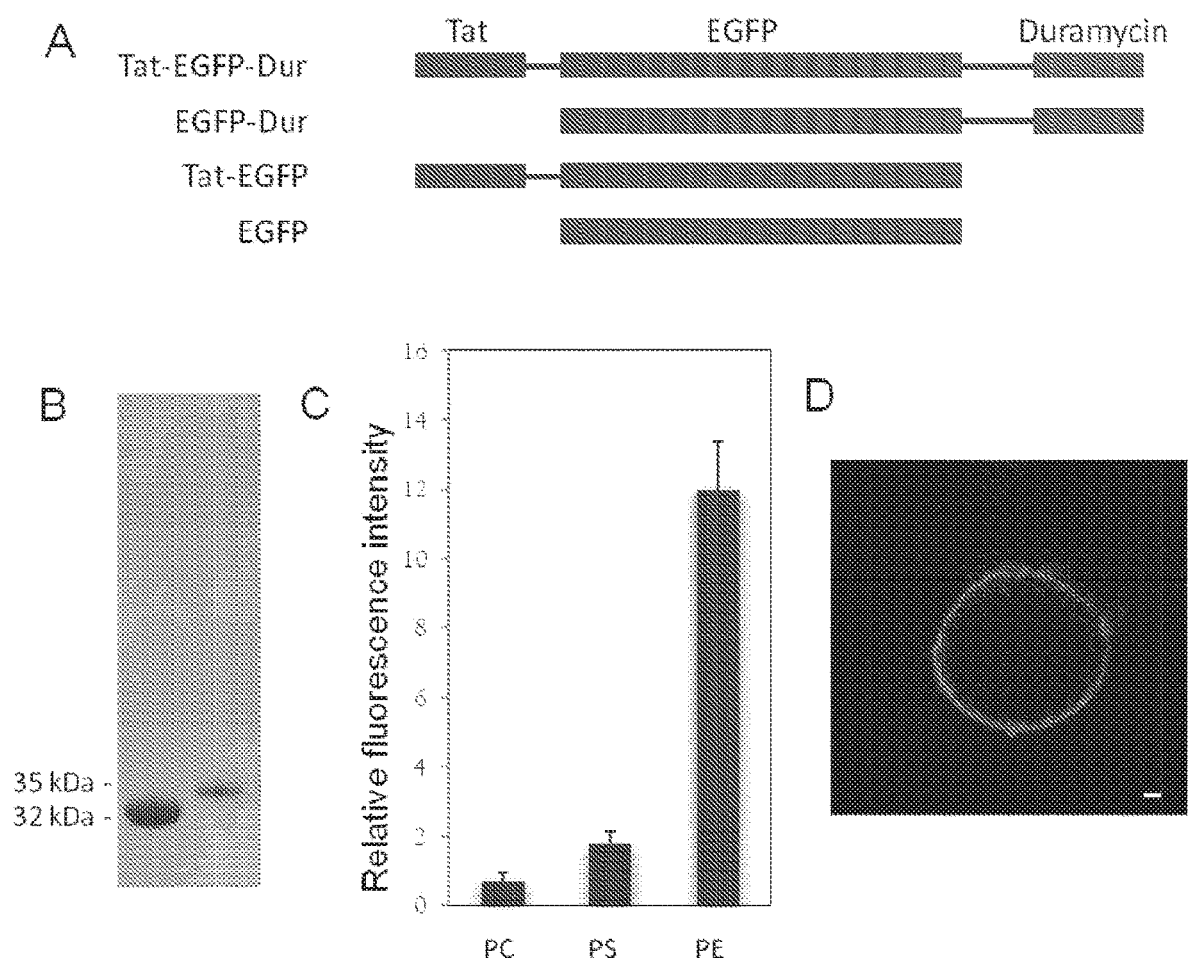
FIG. 1A-D shows the design of exemplary PE probes and cellular staining. (A) Configurations of PE-specific probes composed of EGFP covalently attached to the N-terminal of Duramycin via a $C_{12}$ PEG linker, and with the addition of Tat peptide to the C-terminal of EGFP. Control probes include EGFP and Tat-EGFP, respectively. (B) SDS-PAGE of EGFP (left lane) and EGFP-Dur (right lane). (C) Binding assay for EGFP-Dur using microtiter wells coated with PC, PS and PE. Specific binding occurred with PE but not other phospholipid species. (D) Confocal micrograph of apoptotic a CHO-K1 cell stained with EGFP-Dur; staining from the exterior surface of the plasma membrane but not internal structures. The scale bar represents 2 µm.

As used herein, the terms "extracellular," "extracellular space," and "extracellular region" refer a physical space not contained within a cell, outside a cell, outside of a cell membrane, and/or not contained within a cell membrane. For example, the region immediately adjacent to a cell, but not within the plasma membrane is defined as being extracellular.

As used herein, the terms "intracellular," "intracellular space," and "intracellular region" refer a physical space contained within a cell and/or enveloped within a cell membrane. The "cytoplasmic," "nuclear," "endosomal," and other compartments or organelles within a cell are within the "intracellular space."

DETAILED DESCRIPTION

Provided herein are phosphatidylethanolamine (PE)-specific probes and methods of use thereof In particular, the present invention provides conjugates of PE binding moieties with detectable markers, and methods of use thereof to detect and/or characterize PE within cells.

A. Introduction

Phosphatidylethanolamine (PE) is a major phospholipid in cellular membranes, however, its distribution and functions are yet to be fully characterized. Lantibiotics duramycin and cinnamycin are PE-specific binding agents. Unfortunately, toxicity issues at concentrations compatible to cell biology studies often limit the staining application for these agents.

By nature of their structural features, various phospholipids in cellular membranes contribute to distinct biological roles (van Meer et al. Nat Rev Mol Cell Biol. 2008, 9, 112-124; Kutateladze. Nat Chem Biol. 2010, 6, 507-513; Jean, A. A. Kiger. Nat Rev Mol Cell Biol. 2012, 13, 463-470; Kay & Grinstein. Adv Exp Med Biol. 2013, 991, 177-193; Yeung et al. Science. 2008, 319, 210-213; Vance & Tasseva. Biochim Biophys Acta. 2013, 1831, 543-554; herein incorporated by reference in their entireties).These processes are determined by the spatial and temporal distribution of phospholipids among cellular compartments.

Phosphatidylethanolamine (PE) is a zwitterionic aminophospholipid at physiological pH, with a relatively small ethanolamine headgroup. PE is the second most abundant phospholipid in mammalian cells and the principal phospholipid in bacteria. In mammalian cells, the biosynthesis of PE takes place predominantly at the ER and the inner membrane of mitochondria (Wang et al. Proc Natl Acad Sci U.S.A. 2014, 111; herein incorporated by reference in its entirety). PE is involved in a wide range of cellular activities, where it participates in membrane trafficking and as a precursor in synthetic pathways for other phospholipids and bioconjugates (Wang et al. Proc Natl Acad Sci U.S.A. 2014, 111; Tatsuta et al. Trends Cell Biol. 2014, 24, 44-52; Sebastian et al. Biochim Biophys Acta. 2012, 1821, 1068-1077; Bogdanov et al. Biochim Biophys Acta. 2014, 1843, 1475-1488; Menon & Stevens. J Biol Chem. 1992, 267, 15277-15280; Hanada et al. FEBS Lett. 2009, 583, 1078-83; herein incorporated by reference in their entireties). The physiochemical properties of PE are implicative of utilities in modulating membrane curvature and fusion and are thought to play important roles in maintaining proper folding of membrane proteins (Bogdanov et al. Biochim Biophys Acta. 2014, 1843, 1475-1488; Yang and Ding. Biochemistry. 2003, 42, 6631-6635; Siegel & Epand. Biochim Biophys Acta. 2000, 1468, 87-98; herein incorporated by reference in their entireties). Despite its ubiquitous presence, however, the biological roles of PE in mammalian cellular membrane systems remain to be fully defined.

Lantibiotics duramycin and cinnamycin are 19-amino acid peptides that bind the head group of PE with high specificity and affinity (Navarro et al. Biochemistry. 1985 Aug. 13; 24(17):4645-50;

Machaidze & Seelig. Biochemistry. 2003, 42, 12570-12576; Machaidze et al. Biochemistry. 2002, 41, 1965-1971; Aoki et al. J Biochem. 1994, 116, 291-297; Zhao. Amino Acids. 2011, 41, 1071-1079; Zhao et al. J Nucl Med. 2008, 49, 1345-1352; herein incorporated by reference in their entireties). However, it is known that duramycin and cinnamycin exhibit cytotoxicity, where at micromolar concentration they can cause membrane distortion and induce PE translocation (Makino et al. J Biol Chem. 2003, 278, 3204-3209; herein incorporated by reference in its entirety). The toxicity issue has become a limiting factor in the application of these probes, and can complicate study design and data interpretation. Another drawback in the current approach for PE staining is that it is often a 2-step process, involving an initial binding using biotinylated duramycin/cinnamycin, followed by visualization using fluorophore-conjugated avidin. This method is somewhat cumbersome, and also suffers from toxicity where biotinylation does not completely neutralize the cytotoxicity of the lantibiotics.

Experiments were conducted during development of embodiments of the present invention to characterize the distribution of PE in intracellular membrane networks using PE-specific molecular probes. Duramycin is a 19-amino acid peptide that binds the head group of PE with high specificity and affinity (Navarro et al. Biochemistry. 24, 4645-4650 (1985); Zhao et al. J Nucl Med. 49, 1345-1352 (2008);

herein incorporated by reference in their entireties). Duramycin-based PE binding probes were synthesized for microinjection, scrape-loading, Tat peptide-assisted transduction, etc. In some embodiments, such probes provide utility in characterizing the intracellular distribution of PE, the biological roles of this important phospholipid, and allow for elucidation of regulatory mechanisms of PE and other functionally related phospholipid species. In some embodiments, probes are exogenously delivered to characterize the distribution of PE in cells (e.g., live mammalian cells). Experiments demonstrated that the trans-Golgi was the most prominently stained organelle, consistent with the trans-Golgi network (TGN) being an important component in membrane trafficking. While PE biosynthesis takes place in both ER and mitochondria, only the former was stained positive for PE from the cytosolic surface. This was in line with a scrambled PE distribution in the ER membrane, but sequestration at the inner membrane of the mitochondria. The autophagosomal membrane was positive for PE as it provides a reactive surface for the covalent conjugation of protein factors. The cytosolic surface of early endosomes was homogeneously stained, whereas the luminal side had a granulated pattern which resembled microdomains. The nuclear membrane was strongly stained from the luminal but not the cytosolic side, indicative of an asymmetric PE distribution across the bilayer. Dual staining for PE and phosphatidylserine (PS) revealed drastically different patterns. The data were indicative of differential regulatory mechanisms for these synthetically linked but structurally and functionally distinct aminophospholipids. The plasma membrane inner surface was negative for either probe, suggesting an impeded access from the cytosol. The live cell staining studies conducted during development of embodiments of the present invention provided visual evidence on the distribution of PE in intracellular membrane networks. The data implicate distinct regulatory processes and functions for PE in cellular physiology.

In some embodiments, the present invention provides PE probes (e.g., probes that bind to PE and are detectable). In some embodiments, a PE probe comprises a PE binding moiety (e.g., small molecule, peptide (e.g., duramycin, cinnamycin, etc.), PE-binding proteins (e.g., PEBP2), etc.) and a detectable moiety (e.g., fluorescent moiety, bioluminescent moiety, radioactive moiety, contrast agent, handle (e.g., biotin, His6, etc.), chromophore, etc.), optionally connected by a linker moiety (e.g., PEG linker, peptide linker, alkyl or substituted alkyl linker, etc.), and optionally further comprising a functional moiety (e.g., localization sequence (e.g., Tat)). In some embodiments, a PE probe is suitable for use in cells (e.g., nontoxic, cell permeable, etc.).

B. PE-Binding Moiety

In some embodiments, a PE probe comprises a PE-binding moiety that has greater affinity for PE than one or more other related entities. In some embodiments, probes bind to PE, but not one or more other phospholipids (e.g., does not bind to one or more other diacylglycerides (e.g., phosphatidic acid, phosphatidylcholine, phosphatidylserine, phosphoinositides (e.g., phosphatidylinositol, phosphatidylinositol phosphate, phosphatidylinositol bisphosphate, phosphatidylinositol triphosphate, etc.), etc.), does not bind to one or more phosphosphingolipids (e.g., ceramide phosphocholine, ceramide phosphorylethanolamine, ceramide phosphoryllipid, etc.). In some embodiments, probes bind to targets with an ethanolamine head group and a hydrophobic tail (e.g., phosphorylethanolamine, phosphatidylethanolamine, etc.). In some embodiments, probes bind to PE, but not one or more other lipids (e.g., one or more fatty acids, glycerolipids, glycerophospholipids, sphingolipids, sterol lipids, prenol lipids, saccharolipids, polyketides, etc.). In some embodiments, a probe is PE-specific.

In some embodiments, the PE-binding moiety is a PE-binding peptide (e.g., duramycin, cinnamycin, etc.). In some embodiments, the PE-binding moiety is duramycin (CANSCSYGPL TWSCDGNTK; SEQ ID NO:1). In some embodiments, the PE-binding moiety is a peptide having greater than 50% sequence identity (e.g., >50%, >60%, >70%, >80%, >90%) with duramycin (SEQ ID NO:1) and capable of selectively binding PE. In some embodiments, the PE-binding moiety is a peptide having less than 100% sequence identity (e.g., <95%, <90%, <85%, <80%, <75%, or less) with duramycin (SEQ ID NO:1) and capable of selectively binding PE. In some embodiments, the PE-binding moiety is a peptide having greater than 50% sequence similarity (e.g., >70%, >75%, >80%, >85%, >90%) with duramycin and capable of selectively bonding PE. In some embodiments, the PE-binding moiety is a peptide is 5-50 amino acids in length (e.g., 5, 10, 11, 12, 13, 14, 15, 16, 17, 18, 19, 20, 21, 22, 23, 24, 25 26, 27, 28, 29, 30, 35, 40, 45, 50, or any suitable ranges therein (e.g., 15-25, 12-28, 15-21, 18-35, etc.).

C. Detectable Moiety

In some embodiments, a PE probe comprises detectable moiety (e.g., that can be detected within cells. Any suitable detectable moiety finds use in certain embodiments, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent moiety (e.g., bioluminescent (e.g., photoprotein, luciferase (e.g., renilla, firefly, etc.), etc.), phosphorescent or chemiluminescent label), or a fluorescent moiety (e.g., fluorescent protein (e.g. green fluorescent protein (GFP), enhanced GFP (EGFP), yellow fluorescent protein (YFP), cyan fluorescent protein (CFP), etc.), fluorophore (e.g., xanthene derivatives, cyanine derivatives, etc.).

In some embodiments, the detectable moiety is a peptide or protein (e.g., conjugated or fused directly or indirectly to a PE-binding moiety). In some embodiments, the detectable moiety is a protein or peptide that exhibits or catalyzes light emission (e.g., fluorescence, luminescence, etc.) under appropriate conditions (e.g., when exposed to light at an excitation wavelength, upon contacting a substrate, etc.). In some embodiments, a detectable moiety is a fluorescent protein, such as: blue fluorescent proteins (e.g., TagBFP, mTagBFP, mTagBFP2, Azurite, EBFP2, mKalamal, Sirius, Sapphire, T-Sapphire, etc.), cyan fluorescent proteins (e.g., CFP, Cerulean, SCFP3A, mTurquoise, mTurquoise2, monomeric Midoriishi-Cyan, TagCFP, mTFP1, etc.), green fluorescent proteins (e.g., GFP, EGFP, Emerald, Superfolder GFP, Monomeric Azami Green, TagGFP2, mUKG, mWasabi, Clover, mNeonGreen, etc.), yellow fluorescent proteins (e.g., EYFP, YFP, Citrine, Venus, SYFP2, TagYFP, etc.), orange fluorescent proteins (e.g., mKOK, mKO2, mOrange, mOrange2, etc.), red fluorescent proteins (e.g., mRaspberry, mCherry, mStrawberry, mTangerine, tdTomato, TagRFP, TagRFP-T, mApple, mRuby, mRuby2, etc.), far-red fluorescent proteins (e.g., mPlum, HcRed-Tandem, mKate2, mNeptune, NirFP, etc.), near-IR fluorescent proteins (e.g., TagRFP657, IFP1.4, iRFP, etc.), long stokes shift fluorescent proteins (e.g., mKeima Red, LSS-mKatel, LSS-mKate2, mBeRFP, etc.), photoactivatible fluorescent proteins (e.g., PA-GFP, PAmCherryl, PATagRFP, etc.), photoconvertible fluorescent proteins (e.g., Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange, etc.), photoswitchable fluorescent proteins (e.g., Dronpa), etc.

D. Functional Moieties

In some embodiments, a probe comprises a PE-binding moiety, detectable moiety, and one or more additional functional moieties, such as, for example, localization signals (e.g., nuclear localization sequence (e.g., Tat), cellular localization signal, etc.), targeting moiety, solubilization moiety, cleavable moiety, second detectable moiety (e.g., to create a probe detectable by multiple methods), a handle or tag (e.g., biotin), a therapeutic (e.g., allowing targeting of a therapeutic to PE-rich sites), a surface, a peptide, an antibody, etc.

E. Linker Moiety

In some embodiments, the various moieties (e.g., PE-binding moiety, detectable moiety, functional moiety, etc.) are directly conjugated, tethered, fused, etc. (e.g., via covalent bond). In other embodiments, two moieties (e.g., PE-binding moiety, detectable moiety, functional moiety, etc.) are conneted by a suitable linker (e.g., peptide linker, PEG linker, alkyl or substituted alkyl linker, etc.). The present invention is not limited to any particular linker moiety. In some embodiments, the linker connects two moieties (e.g. PE-binding moiety and detectable moiety). In some embodiments, the linker moiety covalently connects two moieties. In some embodiments, a linker moiety is cleavable (e.g., chemically cleavable, enzyme cleavable, etc.), such that exposure to appropriate conditions (e.g., cleaving enzyme) cleaves the linker moiety and separates the connected moieties. In some embodiments, the linker moiety is a covalent linkage that is: linear, branched, cyclic, heterocyclic, saturated, unsaturated, or various combinations thereof In some embodiments, the linker comprises 1-100 non-hydrogen atoms (in addition to hydrogen atoms) selected from the group of C, N, P, O and S (e.g. 1-75, 1-50, 1-40, 1-30, 1-20, 1-10, 1-5, etc.). In some embodiments, the linker comprises any combination of alkyl, ether, thioether, polyether, amine, alkyl, amide, ester, carboxamide, sulfonamide, hydrazide bonds and aromatic or heteroaromatic bonds. In some embodiments, the linker comprises a polymer (e.g. nucleic acid, polypeptide, lipid, or polysaccharide), a peptide linker, a modified peptide linker, a Poly(ethylene glycol) (PEG) linker, a streptavidin-biotin or avidin-biotin linker, polyaminoacids (e.g., polylysine), functionalized PEG, polysaccharides, glycosaminoglycans, dendritic polymers such as described in WO93/06868 and by Tomalia et al. in Angew. Chem. Int. Ed. Engl. 29:138-175 (1990), PEG-chelant polymers such as described in W94/08629, WO94/09056 and WO96/26754, oligonucleotide linker, phospholipid derivatives, alkenyl chains, alkynyl chains, disulfide, or a suitable combination thereof In some embodiments, a linker moiety comprises any covalent or noncovalent molecular connector capable of stably stringing together a first and second moiety (e.g. PE-binding moiety and detectable moiety). One of ordinary skill in the art will further appreciate that the above linkers are not intended to be limiting.

F. Exemplary Probes

In some embodiments, a PE probe (e.g., PE-specific probe (e.g., one that does not bind to PI or PC)) comprises a PE-binding moiety linked (directly or via a linked moiety) to a detectable moiety.

In certain embodiments, both the PE-binding and detectable moieties are peptides, polypeptides, or proteins. For example, the PE-binding moiety is a PE-binding peptide (e.g., duramycin, cinnamycin, etc.) and the detectable moiety is a fluorescent protein. An example of such a probe is EGFP-Dur (See FIG. 1). In some embodiments, such a probe has a linker (e.g., PEG linker) connecting the two moieties. In certain embodiments, such a probe further comprises a functional moiety (e.g. nuclear localization signal) as in Tat-EGFP-Dur. Such probes may adopt any suitable orientation, including, but not limited to:

C-(detectable moiety)-(PE-binding moiety)-N
C-(functional moiety)-(detectable moiety)-(PE-binding moiety)-N
C-(detectable moiety)-(PE-binding moiety)-(functional moiety)-N
C-(detectable moiety)-(functional moiety)-(PE-binding moiety)-N
C-(functional moiety)-(detectable moiety)-(functional moiety)-(PE-binding moiety)-N
C-(functional moiety)-(detectable moiety)-(PE-binding moiety)-(functional moiety)-N
C-(detectable moiety)-(functional moiety)-(PE-binding moiety)-(functional moiety)-N
C-(PE-binding moiety)-(detectable moiety)-N
C-(functional moiety)-(PE-binding moiety)-(detectable moiety)-N
C-(PE-binding moiety)-(detectable moiety)-(functional moiety)-N
C-(PE-binding moiety)-(functional moiety)-(detectable moiety)-N
C-(functional moiety)-(PE-binding moiety)-(functional moiety)-(detectable moiety)-N
C-(functional moiety)-(PE-binding moiety)-(detectable moiety)-(functional moiety)-N
C-(PE-binding moiety)-(functional moiety)-(detectable moiety)-(functional moiety)-N In some embodiments, any of the connections between moieties in above arrangements are direct covalent connections or connected by a linker moiety.

In certain embodiments, one or more of the PE-binding moiety, linker moiety (when present), functional moiety (when present), and detectable moiety are not peptides, polypeptides, or proteins. For example, in some embodiments, as described herein, the detectable moiety and/or functional moiety is a chemical compound, such as a fluorophore, contrast agent, radionuclide, chemical handle. In other embodiments, a detectable moiety and/or functional moiety is a bead, particle, surface, etc.

G. Manufacture

Probes and the moieties they comprise may be produced/synthesized by any suitable methods. In some embodiments, moieties comprising peptides, polypeptides, and/or proteins are produced recombinantly, synthesized, or purchased from a commercial manufacturer. In some embodiments, chemical moieties (e.g., linkers) are purchased from a supplier or synthesized by known chemistries. In some embodiments, two or more moieties are produced separately and then tethered together (e.g., chemically, enzymatically, etc.). In some embodiments, two or more moieties of a probe are produced (e.g., synthesized, expressed, etc.) as a single unit. In some embodiments with two or more peptide, polypeptide, and/or protein moieties, two adjacent moieties are expressed as a fusion. In embodiments comprising non-peptide components, two or more of the various moieties are typically chemically or enzymatically tethered together following synthesis of the individual moieties. The probes of the present invention are not limited by methods of manufacture.

H. Applications

In some embodiments, the probes described herein find use in any applications in which localizing, identifying, characterizing, and or detecting PE is desired. Probes find use:

in vitro, in vivo, extracellularly, intracellularly, in situ, in a whole organism, etc. Probes find use in clinical, therapeutic, diagnostic, and research applications.

In some embodiments, probes of the present invention provide a non-toxic tool (e.g., unlike free duramycin) for delivering a functional moiety (e.g., therapeutic, etc.) and detectable moiety (e.g., fluorescent marker, handle, etc.) to PE.

In some embodiments, the present invention provides methods of localizing PE with an organelle, cell, tissue, organ, subject, etc. In such embodiments, probes are administered and the detectable moiety is detected to determine the location of PE with the organelle, cell, tissue, organ, subject, etc. A suitable detectable moiety is selected for use in the particular application.

In some embodiments, probes described herein are used with other detectable moieties to identify other cellular components (e.g., proteins, lipids, organelles, etc.) that colocalize with PE. In some embodiments, observation of a probe of the present invention in the same cellular or subcellular location as another labeled component indicates colocalization.

In some embodiments, Forster resonance energy transfer (FRET) or bioluminescence resonance energy transfer (BRET) is used to detect binding partners of PE or cellular or subcellular components that colocalize with PE. In some embodiments, energy transfer from another labeled entity to probes of the present invention bound to PE indicates interactions or colocalization between PE and the other component. In other embodiments, energy transfer from probes of the present invention to another labeled entity to probes of the present invention indicates interactions or colocalization between PE and the other component. In embodiments utilizing a second labeled entity (e.g., FRET, BRET, colocalization experiments, etc.), the second entity is labeled with any suitable label, for example, a fluorophore, fluorescent protein, luciferase, spin label, paramagnetic label, etc.

Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc.

Suitable fluorescent proteins include, for example, blue fluorescent proteins (e.g., TagBFP, mTagBFP, mTagBFP2, Azurite, EBFP2, mKalamal, Sirius, Sapphire, T-Sapphire, etc.), cyan fluorescent proteins (e.g., CFP, Cerulean, SCFP3A, mTurquoise, mTurquoise2, monomeric Midoriishi-Cyan, TagCFP, mTFP1, etc.), green fluorescent proteins (e.g., GFP, EGFP, Emerald, Superfolder GFP, Monomeric Azami Green, TagGFP2, mUKG, mWasabi, Clover, mNeonGreen, etc.), yellow fluorescent proteins (e.g., EYFP, YFP, Citrine, Venus, SYFP2, TagYFP, etc.), orange fluorescent proteins (e.g., mKOK, mKO2, mOrange, mOrange2, etc.), red fluorescent proteins (e.g., mRaspberry, mCherry, mStrawberry, mTangerine, tdTomato, TagRFP, TagRFP-T, mApple, mRuby, mRuby2, etc.), far-red fluorescent proteins (e.g., mPlum, HcRed-Tandem, mKate2, mNeptune, NirFP, etc.), near-IR fluorescent proteins (e.g., TagRFP657, IFP1.4, iRFP, etc.), long stokes shift fluorescent proteins (e.g., mKeima Red, LSS-mKatel, LSS-mKate2, mBeRFP, etc.), photoactivatible fluorescent proteins (e.g., PA-GFP, PAmCherry1, PATagRFP, etc.), photoconvertible fluorescent proteins (e.g., Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange, etc.), photoswitchable fluorescent proteins (e.g., Dronpa), etc.

Suitable luciferases include, for example, Gaussia, Gaussia-Dura, Cypridina, Renilla, and firefly.

In some embodiments, probes are useful for delivering a functional moiety (e.g., a therapeutic, a binding element for another cellular entity, etc.) to cellular regions (or regions in tissue) that are rich in PE.

In some embodiments, the probes are useful for locating, identifyinh, characterizing, etc. membrane vesicles (e.g., PE-containing vesicles), such as microparticles, exosomes and intraluminal vesicles (ILVs).

In some embodiments, systems, devices, or apparatuses for assessing, quantitating, detecting, and/or monitoring the compositions, methods, and/or assays described herein are provided. In some embodiments, systems, devices, and/or apparatuses are provided to detect, quantitate, locate, characterize or monitor PE (e.g., via a PE probe). Devices, systems or apparatuses are provided comprising one or more of a spectrophotometer, fluorometer, luminometer, photomultiplier tube, photodiode, nephlometer, photon counter, electrodes, ammeter, scintillation counter, Geiger counter, voltmeter, capacitative sensors, radio-frequency transmitter, magnetoresistometer, flow cytometer, CCD, Hall-effect device, etc. In some embodiments, a device suitable for detection of a given detectable moiety (e.g., fluorescent protein, luciferase, beta lactamase, or radiolabel) is selected and/or provided.

The applications described herein are exemplary and should not be viewed as limiting.

EXPERIMENTAL

Example 1

Figure 8:
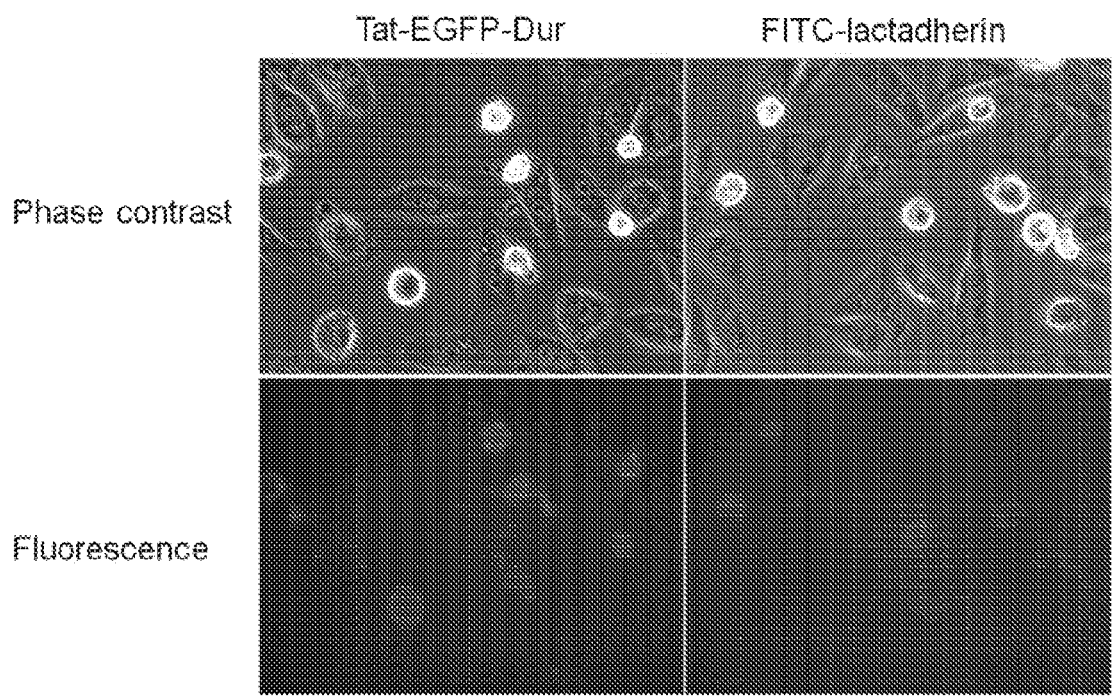
FIG. 8 shows confocal micrographs of viable cells demonstrating the absence of probe binding at the cell surface (in contrast to FIG. 1D).

Duramycin-based probes were constructed, for example, to investigate the intracellular distribution of PE (See, e.g., FIG. 1A). For example, Duramycin was covalently conjugated, via the N-terminus through a $C_{12}$ polyethylene glycol (PEG), to the C-terminus of enhanced green fluorescence protein (EGFP-Dur). A second probe was synthesized with an additional Tat peptide fused to the N-terminus of EGFP (Tat-EGFP-Dur). Control probes were EGFP and Tat-EGFP, respectively. The conjugation products were examined by SDS-PAGE (FIG. 1B), and PE binding specificity was validated using microtiter plates coated with various phospholipids including phosphatidylcholine (PC), PS and PE. Duramycin-conjugated EGFP binds specifically to PE, but not PS or PC (FIG. 1C). When incubated with apoptotic cells in culture, the probe bound to the outer surface of the plasma membrane and was not internalized, which was consistent with the externalization of PE (FIG. 1D). In contrast, there was no binding at the surface of viable cells (FIG. 8). These studies served as an independent validation for the specific binding to PE-containing cellular membranes.

Figure 2:
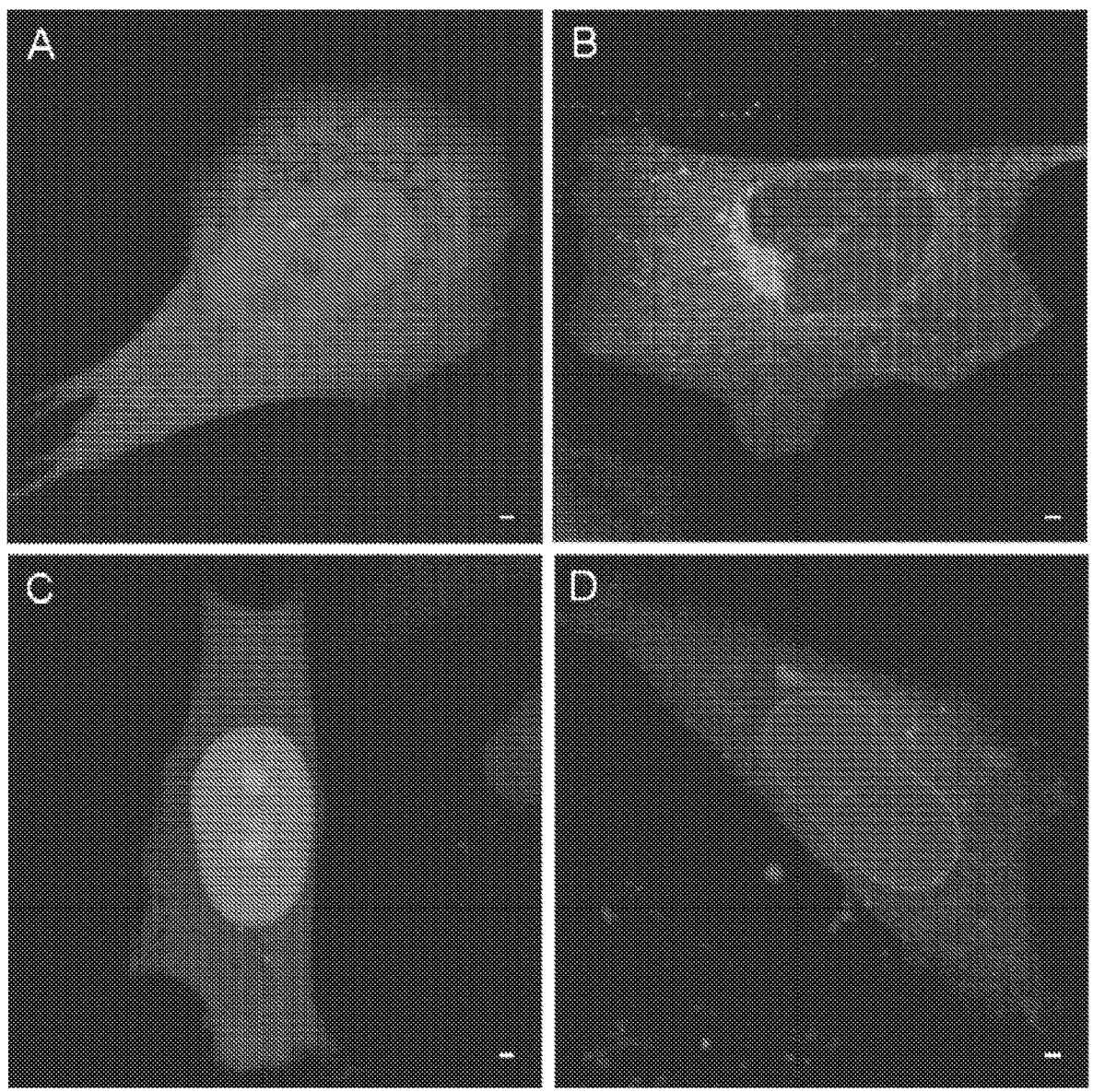
FIG. 2A-C shows confocal micrographs of CHO-K1 cells microinjected with probes. (A) Microinjected EGFP as a control distributed diffusely inside the cell without discernible staining patterns but void spaces where the dye had no access to. (B) A CHO-K1 cell with microinjected EGFP-Dur; prominent staining of juxtanuclear structures and an expansive membrane network in the cytosol. (C) Tat-EGFP as a control was microinjected and translocated into the nucleus. (D) A CHO-K1 cell microinjected with Tat-EGFP-Dur. Note the nuclear translocation of the probes and staining of the nuclear membrane by Tat-EGFP-Dur presumably from the inner membrane surface. The sale bars represent 2 µm.

When EGFP alone as a control was microinjected into viable Chinese hamster ovarian (CHO-K1) cells, it revealed no discernible structures, but was distributed diffusively inside the cell with voids, indicating the cellular compartments that are inaccessible from the cytosol (FIG. 2A). In contrast, microinjected EGFP-Dur stained intracellular membrane networks with distinct patterns (FIG. 2B). The binding was particularly intense at a juxtanuclear membrane complex. Intracellular vesicular structures and an extensive mesh of intracellular membrane network which covered most of the cytosol were also strongly stained. No signal was detected at the nuclear membrane. Unexpectedly, the plasma membrane was essentially negative.

The nuclear membrane was not stained by EGFP-Dur from the cytosolic side, which was indicative that PE was either present in low abundance in the nuclear envelop or sequestered in the inner leaflet of the bilayer. In order to gain access to the luminal face of the nuclear membrane, a probe was needed that could target the nucleus. The HIV Tat peptide encodes a nuclear localization signal. The addition of Tat to the N-terminal of EGFP resulted in a marked redistribution to the nucleus, demonstrating the nuclear localization effect of Tat peptide (FIG. 2C). Using a nuclear localizing PE probe (Tat-EGFP-Dur) resulted in a conspicuous staining of the nuclear membrane (FIG. 2D). This was accompanied with a reduction of cytosolic signal, consistent with the nuclear translocation of bulk of the probe. The differential staining with nuclear localization of the PE probe suggested PE being asymmetrically distributed to the luminal surface of the nuclear membrane bilayer, and that a greater PE pool was accessible from inside the nucleus but not from the cytosolic side.

Figure 3:
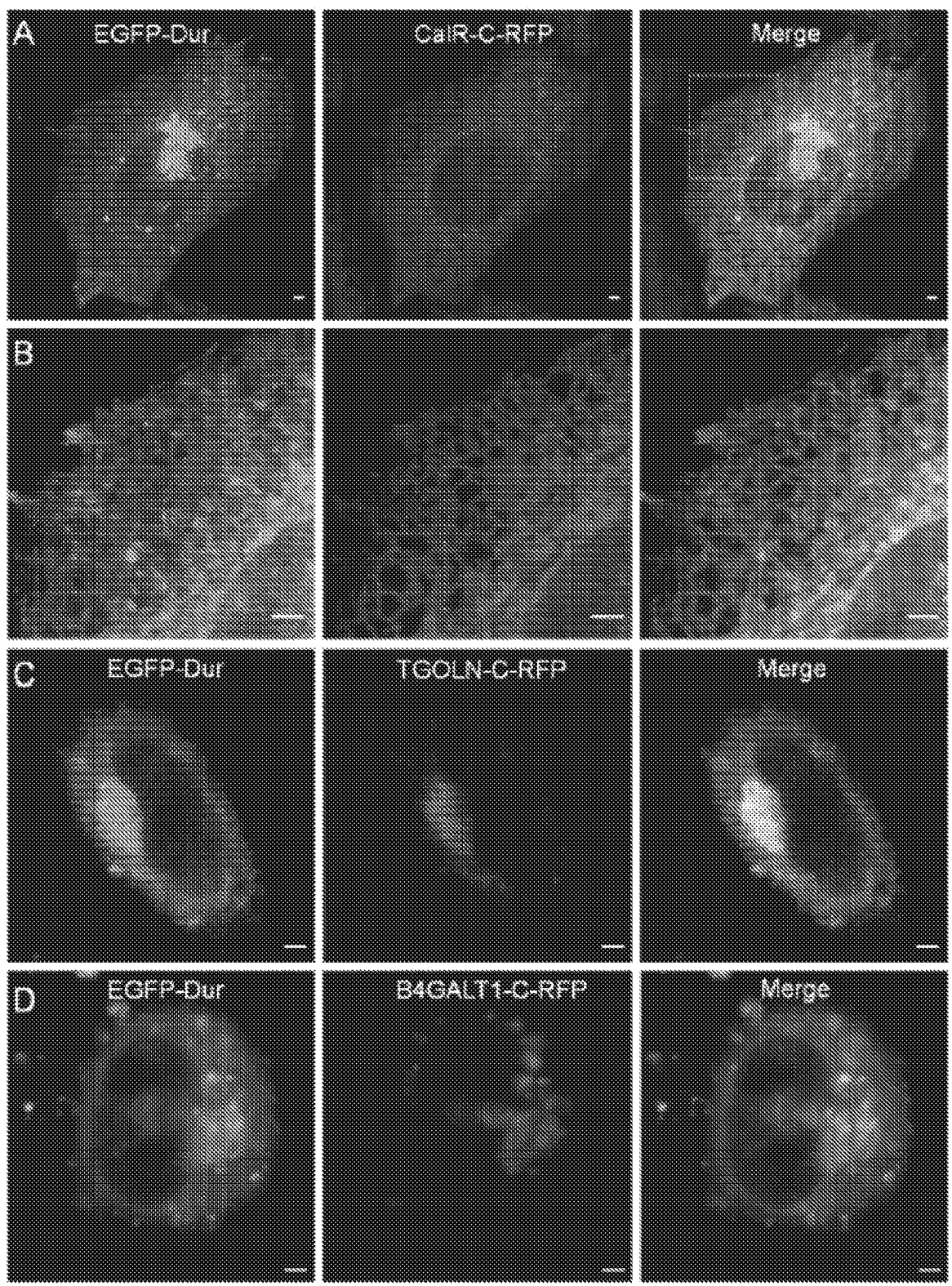
FIG. 3A-D shows staining for PE distribution at the ER and Golgi. (A) Confocal micrographs of a representative CHO-K1 cell microinjected with EGFP-Dur and colocalization with an endogenously expressed ER marker (CalR-C-RFP). (B) Magnified regional micrographs demonstrating the colocalization between PE staining and the ER marker. (C) Colocalization between PE staining using EGFP-Dur with an endogenously expressed marker for trans-Golgi (TGOLN-C-RFP). (D) Co-staining between EGFP-Dur and a cis-Golgi marker (B4GALT1-C-RFP). The sale bars represent 2 µm.
Figure 9:
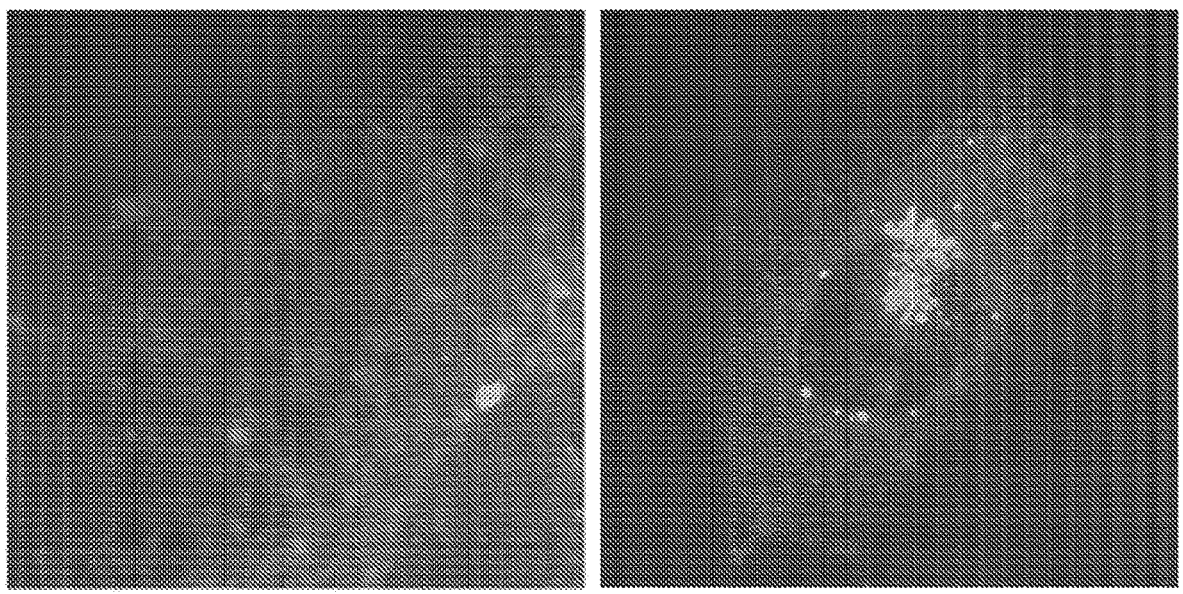
FIG. 9 shows images depicting colocalization of PE-specific probe with the ER membrane network.

The final step of PE biosynthesis from CDP-ethanolamine and diacylglycerol takes place in ER membranes (Vance & Tasseva. *Biochim Biophys Acta.* 1831, 543-554 (2013); herein incorporated by reference in its entirety). An ER-specific marker, calnexin, was expressed fused with RFP (CalR-C-RFP), in CHO-K1 cells. The marker delineated the ER as an extensive membrane network in the cytosol. Staining for PE using GFP-Dur after microinjection revealed a substantial coregistration with the ER membrane network (FIGS. 3A-B, and FIG. 9). The signal intensity at the ER was significant and consistent throughout the entire ER network. These results provided visual evidence that PE was present at appreciable levels and was accessible from the cytosolic side of ER.

The Golgi apparatus plays a central role in sorting and transportation of proteins and membranes. There involves extensive membrane reorganization. Prior evidence indicates that aminophospholipids such as PS and PE are translocated to the cytosolic leaflet of Golgi membrane by P4 ATPases (Sebastian et al. *Biochim Biophys Acta.* 1821, 1068-1077 (2012); herein incorporated by reference in its entirety). Additionally, PE functions as molecular chaperons in preserving the correct topology of membrane proteins (Bogdanov et al. *J Biol Chem.* 274, 12339-12345 (1999); herein incorporated by reference in its entirety). Therefore, experiments were conducted during development of embodiments of the present invention to examine the colocalization of PE-binding probe with the Golgi complex. A trans-Golgi network (TGN) marker, trans-Golgi network protein 2 (TGOLN2) fused with RFP, was expressed in CHO-K1 cells to highlight the TGN. EGFP-Dur bound intensely to a membrane network near the nucleus, which coregistered with the TGN marker (FIG. 3C). Based on the signal intensity of binding, there was a significance presence of PE on the cytosolic side of Golgi complex, and it reflected a selective translocation of PE to the cytosolic side of trans-Golgi membrane. The distribution of EGFP-Dur in cells that express a cis-Golgi marker, B4GALT1-C-RFP, resulted in a significant colocalization but with less signal intensity (FIG. 3D).

Figure 4:
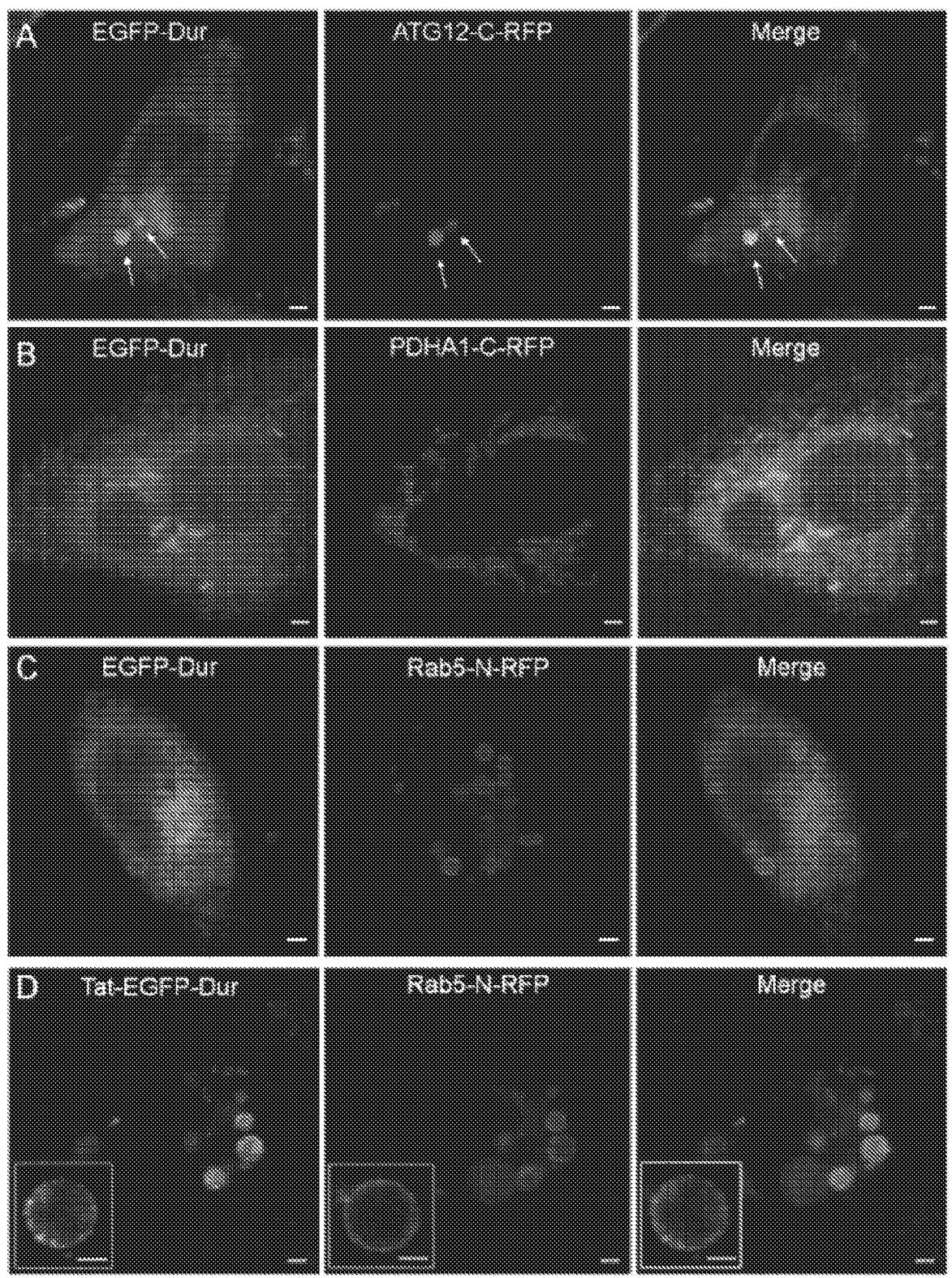
FIG. 4A-D shows PE staining at autophagosomes, mitochondria and endosomes. (A) Co-staining of PE using microinjected EGFP-Dur and endogenously expressed autophagosome marker (ATG12-C-RFP). (B) Co-staining of PE using scrape-loaded EGFP-Dur with an endogenously expressed marker for mitochondria (PDHA1-C-RFP). (C) Co-staining of PE using scrape-loaded EGFP-Dura and endogenously expressed marker for early endosomes (Rab5-N-RFP); PE staining took place from the cytosolic membrane surface of endosomes. (D) Staining of the luminal membrane surface of endosomes using Tat-EGFP-Dur and the colocalization with an endogenously expressed early endosomal marker (Rab5-N-RFP). A magnified regional view of a representative endosome micrograph is shown in insets. Punctuate appearance of PE-positive structureslining the inner surface of endosomes whereas the Rab5-based endogenous marker stained the cytosolic membrane surface. The sale bars represent 2 µm.

Autophagy is an important catabolic mechanism for cells to salvage intracellular components (Maiuri et al. *Nat Rev Mol Cell Biol.* 8, 741-752 (2007); herein incorporated by reference in its entirety). The process involves the formation of membrane-bound vesicles in the cytosol which ultimately fuse with lysosome for degradation. The microtubule-associated protein 1A/B-light chain 3 (LC3), a mammalian homolog of yeast Atg8, is essential for the formation of autophagosomes. LC3 is a cytosolic protein that is covalently attached to PE in autophagosomal membranes via ubiquitin-like conjugation (Hanada et al. *FEBS Lett.* 583, 1078-1083 (2009); herein incorporated by reference in its entirety). Experiments were conducted during development of embodiments of the present invention to investigate if PE was readily available as conjugation targets in autophagosomal membranes. By endogenously expressing an autophagosomal marker, Atg12 fused with RFP, a focal staining pattern was observed for PE by GFP-Dur, which colocalized with autophagosomes (FIG. 4A). A positive PE staining in autophagosomal membranes was consistent with the role of PE as a source of conjugation targets in mediating membrane trafficking in the autophagosomal cascade.

PS is imported to the mitochondria via mitochondria-associated membranes. The inner membrane of mitochondria is an important venue for PE biosynthesis from PS by phosphatidylserine decarboxylase (PSD) (Vance et al. *Biochim Biophys Acta.* 1831, 543-554 (2013); van Meer et al. *Nat Rev Mol Cell Biol.* 9, 112-224 (2008); herein incorporated by reference in their entireties). Staining using EGFP-Dur did not show a consistent colocalization with an endogenously expressed mitochondria marker, pyruvate dehydrogenase alpha 1 fused to RFP (PDHA1-C-RFP) (FIG. 4B). This observation was consistent with PSD being localized at the inner membrane of mitochondria and that PE once synthesize was sequestered and thus was inaccessible from the cytosolic side.

The endosomal membrane is bilayered as it is originated from the plasma membrane. PS is present in the cytosolic leaflet of endosomal membrane. Recent evidence suggests that the asymmetric distribution of PS across the bilayer is maintained by P4 ATPase activities, and that PS is inaccessible on the luminal membrane surface (Chen et al. *PLoS. Genet.* 6, (2010); herein incorporated by reference in its entirety). When EGFP-Dur was introduced to the cytosol, significant levels of PE were detected on the cytosolic face of endosomal membrane, as signals coregistered with an endogenously expressed early endosomal marker Rab5-N-RFP (FIG. 4C). Additionally, the incubation of Tat-EGFP-Dur with intact cells resulted in the internalization of the probe in endosomal vesicles, and the probe was confined in endosomal compartments without detectable release into the cytosol. This presented an opportunity to examine the presence/absence of PE at the luminal surface of endosomes. It became apparent that Tat-EGFP-Dur stained the luminal surface of endosomal vesicles. The staining pattern was heterogeneous with small, bright bodies resembling the size and features of microdomains (FIG. 4D). In contrast, endosomal vesicles that engulfed the control probe, Tat-EGFP, appeared as homogenous spheres with fluorescent signal diffused throughout the luminal space. The membrane association of Tat-EGFP-Dur from the luminal side of endosomal vesicles was indicative of an appreciable level of PE. These results indicated a redistribution of PE during and/or after endosomal formation where PE became accessible on the luminal side of the membrane bilayer.

Figure 5:
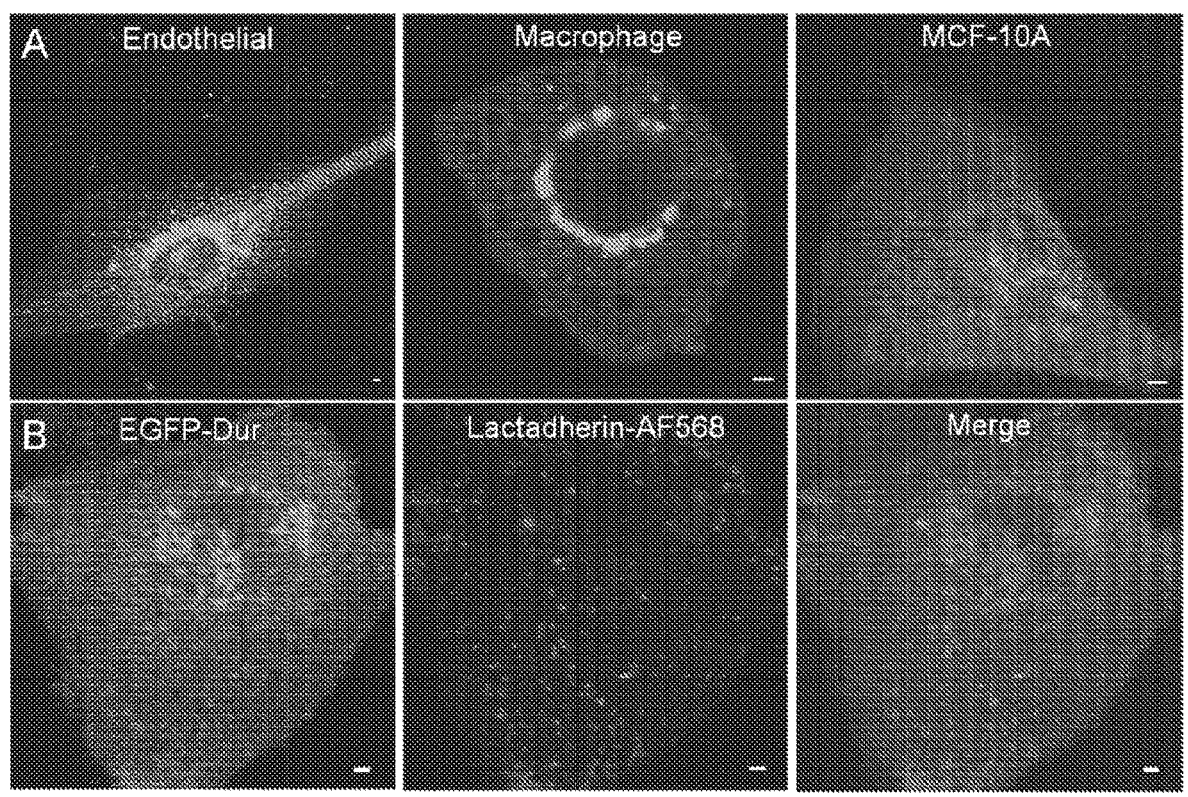
FIG. 5A-B shows intracellular PE staining in different cell types and PE/PS dual staining (A) Confocal micrographs of endothelial (left), macrophage (middle) and epithelial (right) cells microinjected with EGFP-Dur. The staining revealed distinct intracellular morphological features. (B) Confocal micrographs of a CHO-K1 cell microinjected with EGFP-Dur and lactadherin-AF568, which are specific probes for PE and PS, respectively. The sale bars represent 2 µm.
Figure 6:
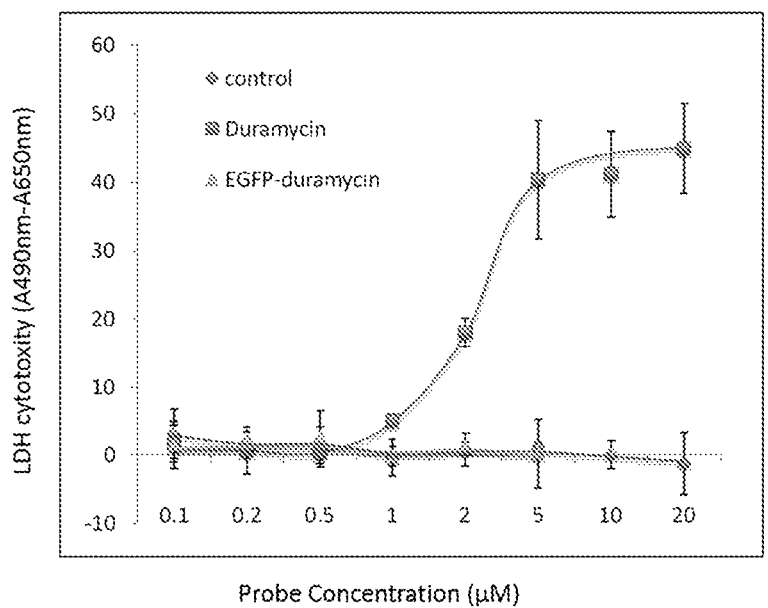
FIG. 6 demonstrates the non-toxicity of EGFP-Dur to cells. Hela cells were treated with the relative peptide or proteins for 24 hours. Cell toxicity was measured with LDH cytotoxicity assay kit
Figure 7:
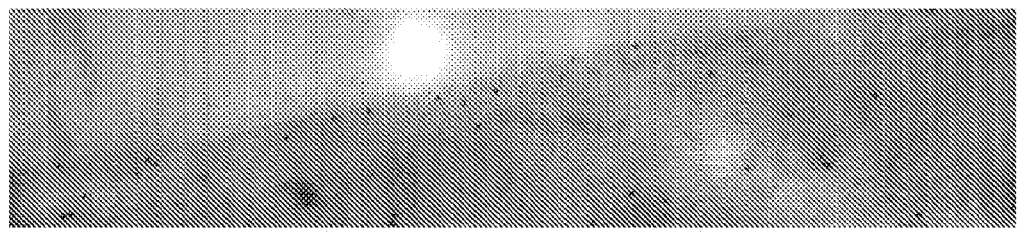
FIG. 7 shows an imaging depicting EGFP-duramycin specifically binding onto the cellular plasma membrane and inna-membrane. CHOK1 cells were prepared as sections for TEM immunostaining Then, cell section was probed with EGFP-duramycin Immunostaing was performed with GFP antibody.

To explore intracellular distribution patterns of PE and to demonstrate the utility of PE staining, additional cell types were included. Microinjection of EGFP-Dur into cultured primary human aortic endothelial cells reveled intense staining of the Golgi and presumably the ER that has a fibrous appearance in parallel with the long axial of the cell (FIG. 5A). In contrast, PE staining of a macrophage demonstrates numerous membrane-bound cytoplasmic structures which resemble vacuoles known to this cell type (FIG. 5A). In an epithelial cell type, MCF-10A, the staining of PE detected again the expansive ER membrane system with prominent Golgi signals at the juxtanuclear region (FIG. 5A). Overall, the figure panels demonstrated utility for characterizing morphological features in intracellular membrane networks that were intrinsic to different cell types.

Existing literature indicates that PS is present at the cytosolic side of the plasma membrane, endosomal vesicles, and to a lesser extent, the TGN (Fairn et al. *J Cell Biol.* 194, 257-275 (2011); herein incorporated by reference in its entirety). Experiments conducted during development of embodiments of the present invention indicated, with direct visual evidence, that the intracellular distribution patterns of PE and PS were different with some overlap. To simultaneously characterize the relative distribution of these two members of aminophospholipids, co-staining was performed by microinjecting a mixture of two different probes at equal concentrations, EGFP-Dur and Lactadherin-Alexa 568, which bound PE and PS, respectively. As shown in FIG. 5B, the most striking difference was that while Lactadherin stained intensely the intracellular vesicles, presumably the endosomal vesicles, there was essentially an absence of binding on the ER. In contrast, the ER was stained brightly and consistently for PE throughout the cytosol. The ER is a major source of newly synthesized PE as well as PS (Vance et al. *Biochim Biophys Acta.* 1831, 543-554 (2013); van Meer et al. *Nat Rev Mol Cell Biol.* 9, 112-224 (2008); herein incorporated by reference in their entireties). PE staining is significant and consistent throughout the ER, whereas PS is virtually undetectable from the cytosolic side using either microinjected probes or endogenously expressed (Fairn et al. *J Cell Biol.* 194, 257-275 (2011); herein incorporated by reference in its entirety). The staining results were indicative of a significant presence of PE in the cytosolic side of ER, but not so for PS. The difference was implicative of differential regulatory processes for the two aminophospholipid species. The TGN was weakly positive for Lactadherin, but stained most prominently for PE. It indicated that the signals from PS staining may have been in part evolved from recycling endosomal membranes, whereas the Golgi membrane contains significant levels of PE accessible from the cytosolic side. Given its unique physicochemical properties, PE has been implicated in membrane fusion and formation of membrane curvatures (Allen et al. *Biochemistry.* 29, 2976-2985 (1990); herein incorporated by reference in its entirety). PE is essential as chaperons for maintaining proper folding of membrane proteins (Bogdanov, M., Umeda, M., Dowhan, W. Phospholipid-assisted refolding of an integral membrane protein. Minimum structural features for phosphatidylethanolamine to act as a molecular chaperone. *J Biol Chem.* 274, 12339-12345 (1999); herein incorporated by reference in its entirety). The prominent PE staining at the TGN was consistent with an active role of the Golgi in protein sorting and membrane trafficking.

Evidence substantiates that PE has a significant presence at the inner leaflet of the plasma membrane (Vance et al. *Biochim Biophys Acta.* 1831, 543-554 (2013); van Meer et al. *Nat Rev Mol Cell Biol.* 9, 112-224 (2008); herein incorporated by reference in their entireties). However, an unexpected finding was that there was a lack of appreciable level of staining at the cytosolic side of the plasma membrane for both PE and PS when probes were microinjected, despite the fact that a number of other organelles were stained positive from the cytosolic side. A negative staining outcome at the plasma membrane raised two possibilities. The first scenario was that the physical orientation and/or packing of PE in the cytosolic leaflet rendered it unrecognizable by the probe, whereas this did not happen in the ER, endosomes, Golgi or the luminal surface of the nucleus. A second possibility was that in a viable, structurally intact cell, the cytosolic surface of the plasma membrane was shielded by cytoskeletal and/or other structural elements, thus making it less accessible for exogenous probes. There has been evidence where the plasma membrane inner surface may be a compartmentalized space where cytosolic factors have an impeded access to cytoskeletal components (Sayner et al. *Am J Physiol Lung Cell Mol Physiol.* 301, L117-124 (2011); herein incorporated by reference in its entirety). It is recognized that the outcome of a probe-based staining approach reflects not only the intrinsic localization of the target, but also physical distribution of the probe. The use of exogenous probes provides a snap shot of what is accessible from the probe's perspective; and this information, in turn, has implications in molecular interactions among cellular compartments.

The biological functions of PE in the intracellular membrane network are yet to be fully established. PE is zwitterionic and assumes a cone-shaped structure because of a relatively small head group. The distribution and functions of PE in cellular physiology is dictated by its physicochemical features. PE is known to play a role in membrane reorganization and trafficking, and it is fusogenic. The presence PE in cellular membranes is essential for preserving the correct conformations of membrane proteins. Emerging evidence indicates that the flip-flop of PE across the membrane bilayer serves as a diluting factor for local PS density (Das et al. *Nat Cell Biol.* 14, 304-310 (2012); herein incorporated by reference in its entirety). During the formation of autophagosomes, PE, but not PS, is the sole donor of primary amines for covalently ligating ubiquitin-like protein LC3 to autophagosomal membrane surface for inducing membrane hemifusion (Hanada et al. *FEBS Lett.* 583, 1078-1083 (2009); herein incorporated by reference in its entirety). The intracellular pH is thought to play a determinant role in the selectivity for PE and suppression of conjugation reactions to PS (Oh-oka et al. *J Biol Chem.* 283, 21847-21852 (2008); herein incorporated by reference in its entirety). The physical distribution of PE in organelles and membrane compartments will be an important determinant for its biological functions.

Example 2

Plasmid Construction

A GFP mutant with a single Cys on the C-terminus was constructed by site directed mutagenesis and with GFP as template. The primers used were: cttggctacggccgccagcaaggcggccagggcggccgcggtggatccacc (SEQ ID NO:2) and ggtggatccaccgcggccgccctggccgccttgctggcggccgtagccaag (SEQ ID NO:3). The resulted plasmids were confirmed by sequencing.

Protein Expression, Purification and Conjugation

Duramycin (Sigma-Aldrich D3168) was dissolved in anhydrous dimethylformamide to a concentration of 10 mg/mL and combined with SM(PEG)12-NHS-PEG-maleimide crosslinker (Thermo Scientific #22112) at 1:1 molar concentration. 8 molar equivalents of triethylamine was then added to reaction mixture (RM). RM was vortexed for 30 seconds and reaction was allowed to proceed under coaxial rotation while monitored by High-Performance Liquid Chromatography (HPLC) for formation of conjugates. RM was purified using HPLC [solvent A=0.1% trifuoroacetic acid (TFA) in water; solvent B=0.1% TFA in Acetonitrile. HPLC method—100% A at injection, ramp to 25% B over 15 min, ramp to 55%B over 45 min]. Identity of chemical conjugates was confirmed using molecular weight determination from HPLC fraction samples submitted to mass spectrometry via an Agilent 6520 Q-TOF LCMS system. HPLC yielded 3 peaks corresponding to unconjugated duramycin (32 min peak, MW≈2012 Da), mono-SM(PEG) 12 conjugated duramycin (35.5 min, MW≈2763 Da, and bis-SM(PEG)12 conjugated duramycin (38 min peak, MW≈3514 Da). Mono-SM(PEG)12 conjugated duramycin peak from HPLC was allocated into tubes and lyophilized overnight producing a solid white peptide-like substance which was sealed and stored at −80° C. until time of use.

GFP-Cys was purified from IPTG induced BL21(DE3) pLysS. 500 ml of exponentially growing bacteria was induced with 0.4 mM IPTG for 4 hours at 30° C. After centrifugation, cells were re-suspended into 15 ml of lysis buffer (50 mM $NaH_2PO_4$, 300 mM NaCl, 10 mM imidazole, 1 mg/ml lysozyme, 1 mM PMSF, PH 8.0) and sonicated. Ni-NTA beads (2.5 ml) were added into the supernatants, which were then incubated on a rotator at 4° C. for 1 hour. Thereafter, the mixtures were loaded onto a polypropylene column, washed three times with buffer A (50 mM $NaH_2PO_4$, 300 mM NaCl, 20 mM imidazole, PH 8.0), one time with washing buffer B (50 mM $NaH_2PO_4$, 1 M NaCl, 50 mM imidazole, 0.5% Triton X100, 5 mM TCEP, PH8.0) and another two times with washing buffer A, then, eluted with elution buffers (50 mM $NaH_2PO_4$, 300 mM NaCl, 250 mM imidazole, PH 8.0). The eluted Tat fusion proteins were desalted on a Zeba desalt spin column.

Duramycin was conjugated to a $C_{12}$ linker PEG on the N-terminal. SM(PEG)12 conjugated duramycin aliquots were solubilized in triscarboxyethyl phosphine solution and combined with GFP at a molar ratio of 4:1 overnight under coaxial rotation to yield SM(PEG)12-Duramycin-GFP conjugate. Nonconjugated Duramycin-PEG-Maleimide and other impurities were removed using a Sephadex G50 size exclusion column. The purified products were examined using SDS PAGE for molecular weight and purity.

Confocal Microscopy

Fluorescence images were acquired using a Nikon C2 confocal microscope with 63× and 100× oil immersion objective lenses, and handles simultaneous 3-channel fluorescence and diascopic DIC observation. For the live cell imaging, cells were seeded in 35 mm coverslip glass plate with Hepes-buffered DMEM or F12/DMEM and the plate was transferred to a chamber that was placed in a microscope stage heater set to 37° C.

Protein Phospholipid Overlay Assay

1 μl of aliquots of selected dilutions of phospholipid was spotted on Nitrocellulose membrane and completely dried at room temperature for 1 hour. The membrane was blocked in blocking buffer (50 mMTris-HCl, pH7.5; 150 mM NaCl; 0.1% Tween 20 and 2 mg/ml Fatty acid free BSA) for 1 hour at room temperature. Then, incubate the membrane in the fresh blocking buffer containing 0.1 μg/ml of EGFP-duramycin or EGFP respectively overnight at 4° C. After washing membrane 10 times over 1 hour in TBST (50 mMTris-HCl, pH7.5; 150 mM NaCl; 0.1% Tween 20), the membrane was incubated with a 1:10000 dilution of anti-GFR antibody in blocking buffer for 1 hour. Then, the membrane was washed 10 times over 1 hour in TBST and incubated with a 1:5000 dilution of HRP-conjugated anti-rabbit secondary antibody in blocking buffer. Then, the membrane was washed 10 times over one hour in TBST. Finally, the membrane was used for detecting protein binding by ECL according to manufacturer's instructions.

Apoptosis Assay

Campothecin was added to a final concentration of 6 μM for 20 hours to induce apoptosis in CHO-K1 cells. After that, cells were washed three times with fresh media and stained with PE or PS binding probes. Micrographs were captured using either a Zeiss LSM510 confocal microscope or regular fluorescence microscope.

LDH Toxicity Assay

HeLa cells were seeded into 96-well plate overnight. Cells were treated with duramycin, linearized duramycin control peptide or duramycin-EGFP at specified concentrations for 24 hours. LDH toxicity assay was performed according to a protocol provided by the kit manufacturer. A control peptide was synthesized with identical linear sequence of duramycin without PE binding activities. The peptide was synthesized via the solid phase method on an automated peptide synthesizer, with sequence CKQSCSFG-PLTFVCDGNTK (SEQ ID NO:3).

Microparticle Isolation and Staining

Hela cells were used to produce and isolate microparticles. Overnight cultural media of hela cells were collected. The media was used for centrifuging at 800 g for 10 min, then 1,500 g for 15 min to remove cells and cell debris. The supernatants were centrifuged at 21,000 g for 30 min to get the microparticles.

The isolated microparticles were resuspended in 10 μg/ml of EGFP duramycin or EGFP in PBS for 15min respectively. Then, 30 ml of PBS was added immediately and centrifuged at 21,000 g for 30 min. The pellets were further resuspended by PBS and used for detecting binding signals by a Nikon C2 confocal microscope.

Rat Sperm Staining

Fresh sperms taken from Rat were incubated in HTF (human tuber fluid) buffer (100 mM KCl, 0.2 mM Hepes, 21.4 mM lactate, 2.8 mM glucose, 4.7 mM $MgSO_4$, 1.0 mM pyruvate, 0.37 mM $KH_2PO_4$, 2 mM $CaCl_2$, 10% Fetal bovine serum, PH 7.4) supplemented with 24 mM bicarbonate at 37° C. $CO_2$ incubator for three hours. Then, the capacitated sperms were moved to HTF buffer containing 24 mM bicarbonate and 10 mg/ml of EGFP or EGFP-duramycin for 15 min at 37° C. $CO_2$ incubator. The sperms were washed three times with new HTF buffer by centrifugation and fixed with 4% PFA for 10 min. newly suspended sperms were used for Nikon C2 confocal analysis.

Example 3

Probe Synthesis and Characterization

With 19 amino acids, duramycin is the smallest known polypeptide that has a stable, stereospecific binding pocket. The overall configuration of the peptide is maintained with 4 intramolecular covalent bonds, including 3 lanthionines and 1 lysinoalanine. The PE-binding pocket and membrane-interacting region is encompassed between Phe-7 and hydroxyaspartate-15. There is an N-terminal amine and a second primary amine at Lys-2. This configuration is desirable in that the primary amines are away from the binding pocket, providing sites for covalent modification without directly interfering with the PE-binding pocket.

Figure 10:
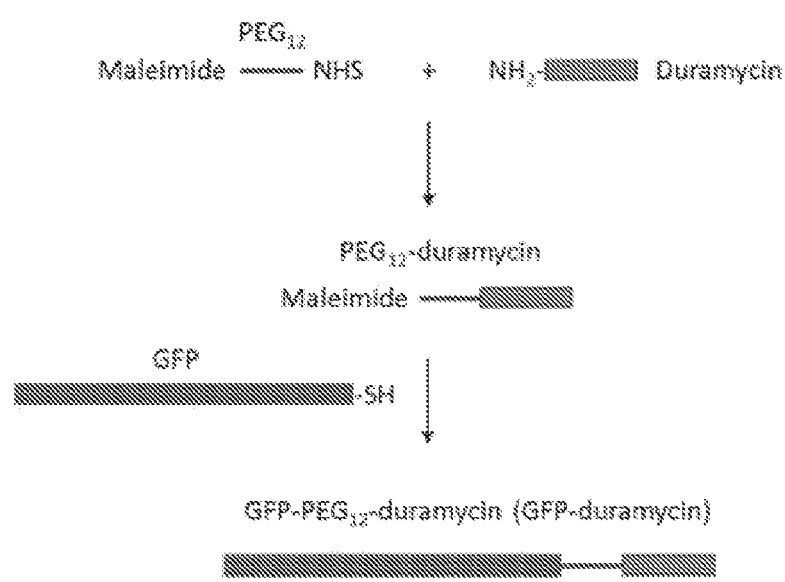
FIG. 10 shows synthesis of duramycin-GFP. Schematic diagram of duramycin-GFP synthesis, with the conjugation of a $C_{12}$ PEG to duramycin via NHS ester chemistry, followed by the covalent attachment of duramycin-PEG in a site-specific fashion to the C-terminus of GFP using maleimide chemistry.

As described above in Example 1, to investigate membrane-bound PE distribution, a duramycin-based probe was constructed. Exemplary construction of the probe is shown in FIG. 10. Duramycin was first covalently conjugated, via the N-terminus to a $C_{12}$ PEG linker, using the N-hydroxysyccinamide ester chemistry which specifically reacts with primary amines at a slightly alkaline condition. Since there are 2 primary amines on duramycin, products of the conjugation reaction included 2 mono-conjugates and 1 species of bis-conjugate, where the molecular weights (2763 and 3514 Da, respectively) were validated using mass spectrometry. In HPLC chromatogram, the mono-conjugate isomers exhibited a split peak with a major and a minor product. It was expected that the reaction to Lys-2 would be the dominant product since the lysine side chain is solvent exposed, whereas the N-terminal amine was somewhat sterically hindered. Since both amines were located away from the binding pocket, these mono-conjugate products were collected and pooled as a single fraction from HPLC elute. The mono-conjugate pegylated duramycin was allowed to react in excess with GFP-Cys, which has a single thiol group on the C-terminus, via maleimide chemistry. The reaction product was processed with Sephadex G-50 gel filtration column to remove nonreacted duramycin conjugates. SDS-PAGE of the final product indicated that the reaction proceeded to completion by depleting free GFP-Cys (FIG. 1B). There was a single band at the expected molecular weight of GFP-duramycin, without signs of degradation or dimmer/multimmer formation. The probe was aliquoted at 1 mg/ml and stored as frozen stock until use.

Binding Activity

Figure 11:
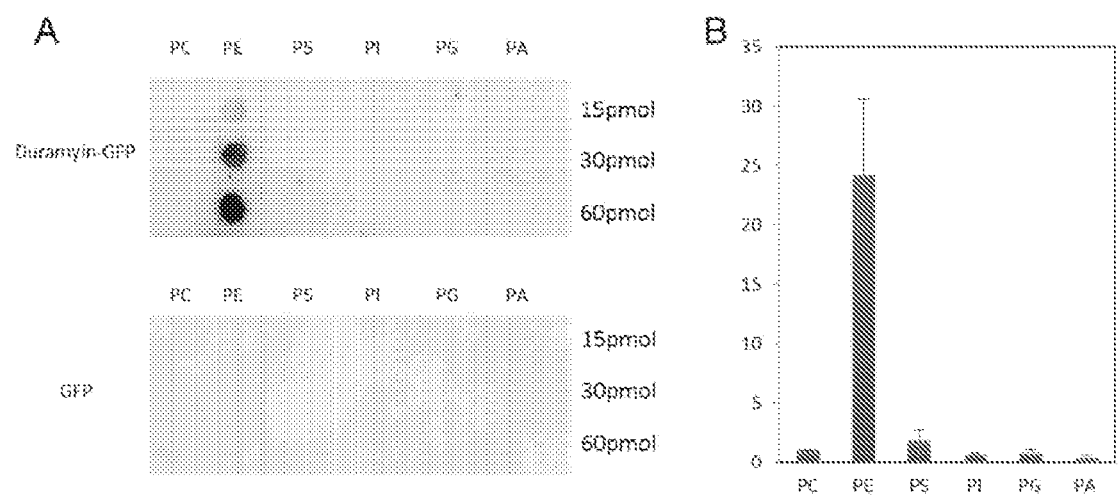
FIG. 11A-B shows a binding assay measuring the interaction of probe to various phospholipids. (A) The protein phospholipid overlay assay was performed by spotting various phospholipids, including PC, PE, PS, PI, PG and PA at 15, 30 and 60 pmol, on Nitrocellulose membrane. The binding of duramycin-GFP to each phospholipid was detected using an anti-GFP primary antibody and then an HRP-conjugated secondary antibody. (B) Relative fold changes in binding to different phospholipid species normalized to the binding level to PC.

PE-binding activity was assessed in binding assays using different phospholipids. As shown in FIG. 11A, the construct bound exclusively to PE, and not to other phospholipids even at relatively high density of lipids. Among these, phosphatidylserine (PS) and phosphatidylcholine (PC) are structural analogs of PE, with a carboxylate and 3 methyl groups, respectively. PC is positively charged, whereas PS, phosphatidylinositol (PI), phosphatidylglycerol (PG) and phosphatidic acid (PA) are negatively charged. Testing with phospholipids that differ in electric charges further demonstrated the minimal nonspecific binding with electrostatic interactions. The relative binding of duramycin-GFP to various phospholipid species at 60 pmol of lipids was quantified using densitometry and the differences in folds were normalized to PC binding (FIG. 11B). These findings are consistent with the structural configuration of the duramycin binding pocket, where the binding cavity is encased in surrounding amino acid backbone and side chains that results in a tight complementarity to the PE head group (Navarro et al. *Biochemistry*. 1985 Aug. 13; 24(17):4645-50; Machaidze & Seelig. *Biochemistry*. 2003, 42, 12570-12576; Machaidze, et al. *Biochemistry*. 2002, 41, 1965-1971; herein incorporated by reference in their entireties). The stereospecific fitting accommodates an embedded PE head group in such a way that there is no room for any additional functional groups. The PEG linker was designed to covalently tether the GFP to duramycin, while being sufficiently long and flexible so that the binding moiety is able to assume optimal orientation toward PE-containing membrane surface.

Toxicity Assay

Figure 12:
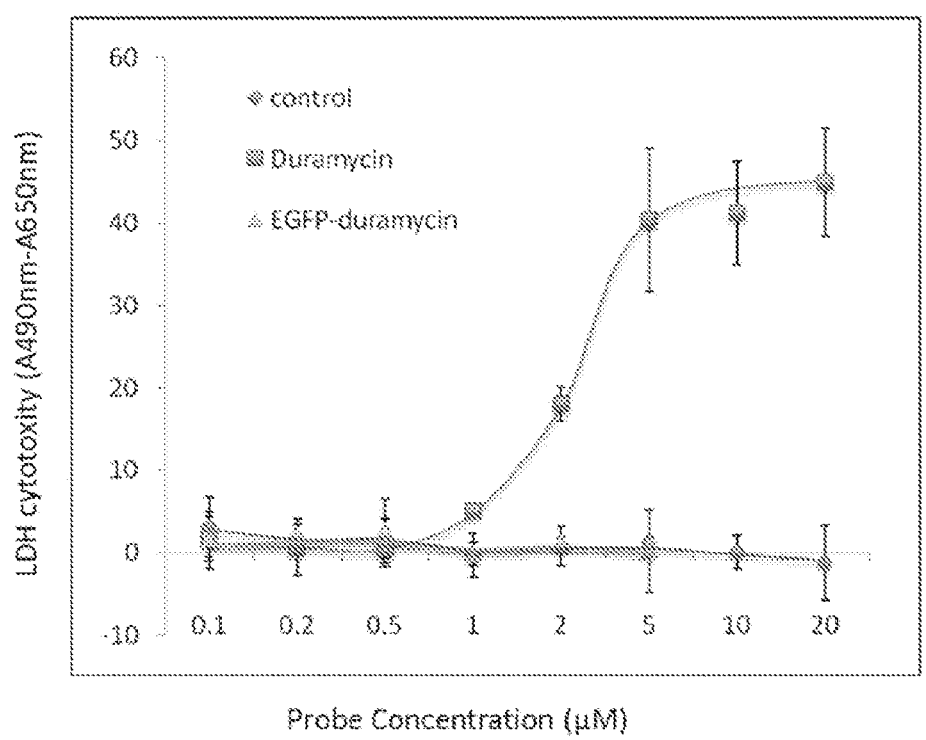
FIG. 12 shows the results of a toxicity study. The release of LDH as a marker for cytotoxicity was assessed in the presence of increasing concentrations of control peptide, which is a linearized duramycin sequence without PE binding activity, duramycin or duramycin-GFP.

A caveat stemming from the binding activities of duramycin/cinnamycin is cytotoxicity (Makino, et al. *J Biol Chem.* 2003, 278, 3204-3209; herein incorporated by reference in its entirety). In their native settings, these lantibiotics are produced and excreted by the host to gain survival advantage by suppressing and killing rival microbes. It has been shown that the binding of these lantibiotics to PE-containing membranes at sufficiently high concentration results in membrane distortion with enhanced transbilayer movement of PE (Makino, et al. *J Biol Chem.* 2003, 278, 3204-3209; herein incorporated by reference in its entirety). As such, cell imaging studies using these lantibiotics are carried out with caution, where the effect of cytotoxicity as an artifact is strictly observed. This concern has limited the wide adaptation of these PE-binding agents. Given this background, we conducted LDH-based toxicity assay comparing the current duramycin-GFP construct with native duramycin and a linearized, inactive peptide which has the linear sequence of duramycin without the stable 3-dimentional configuration. As shown in FIG. 12, the native duramycin caused detectable LDH release in cultured HeLa cells with a concentration at or higher than 2 μM. In contrast, incubation with duramycin-GFP did not result in detectable LDH release at 10 μM, which was the highest concentration tested. This lack of toxicity was identical with the linearized, inactive control peptide. Note the LDH release assay was conducted with 24-hour incubation. Given that most cell imaging studies involve a staining process that lasts on the order of minutes, these data ensured that cytotoxicity as an artifact is a nonissue for the current construct compared to native duramycin. These findings indicated that duramycin loses its cytotoxicity when conjugated to a macromolecule on the N-terminal, while retaining PE binding activity.

Cell Imaging Studies

Figure 13:
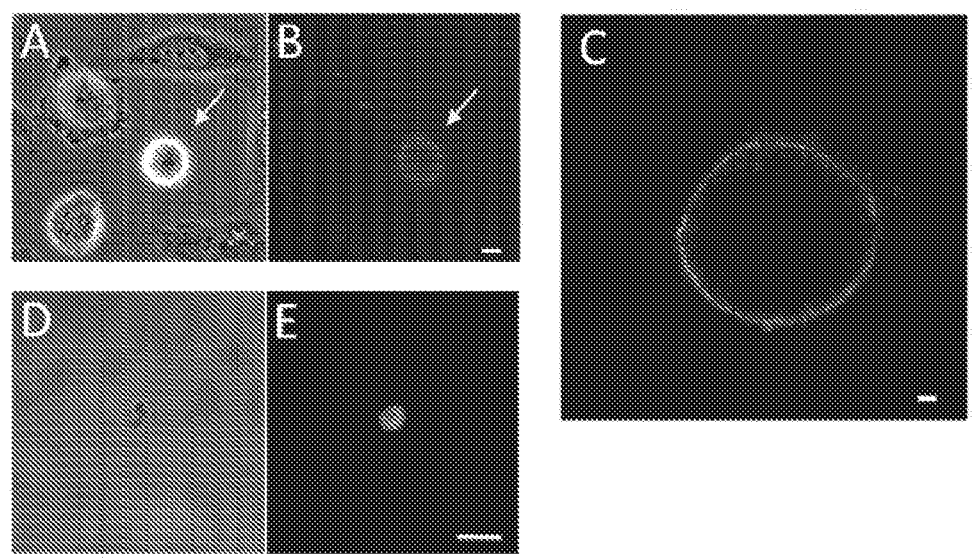
FIG. 13A-E shows images of cell staining studies. (A-B). Phase contrast and fluorescent micrographs of cultured CHO-K1 cells treated with Campothecin to induce apoptosis. Scale bar=10 µm. Duramycin-GFP stained positively on cells that apoptotic but not viable cells. (C) Confocal micrograph of an apoptotic cell stained with duramycin-GFP, where the signal is on the outer surface of the cell membrane without internalization. Scale bar=2 µm. (D-E) Phase contrast and confocal images of a microparticle isolated from cultured breast cancer cells stained with duramycin-GFP. Scale bar=2 µm.

Utility of the current PE-binding probe was demonstrated in a series of cell imaging studies. In a viable, resting mammalian cell, PE is sequestered in the inner leaflet of the plasma membrane by putative energy-dependent translocases which are members of the P4 ATPase family. In apoptotic cell, the internal cellular destruction is accompanied with a loss of symmetric distribution of aminophospholipids, thus PS and PE become externalized to the cell surface (Martin et al. *J Exp Med.* 1995, 182, 1545-1556; Emoto et al. *Umeda. Exp Cell Res.* 1997, 232, 430-434; herein incorporated by reference in their entireties). While the externalized PS is recognized by well-defined receptors on the surface of immune cells as a "eat me" signal, the role of PE flip-flop is yet to be clearly defined (Shiratsuchi et al. *Biochem Biophys Res Commun.* 1998, 246, 549-555; herein incorporated by reference in its entirety). Surface PE provides another molecular marker for identifying dead and dying cells. An advantage of PE compared to PS is that PE is the dominant species and its externalization gives rise to a greater density of binding targets. In this sense, PE provides a more conspicuous marker for detecting dead and dying cells. As shown in FIGS. 13A-C, duramycin-GFP stained strongly the outer surface of dead and dying cells, with no detectable staining either on viable cells or in intracellular components of apoptotic cells.

Cancer cell-derived microparticles (MPs) are vehicles that carry signaling cargos and play important regulatory roles in intercellular communications (Muralidharan-Chari et al. *J Cell Sci.* 2010, 123, 1603-1611; herein incorporated by reference in its entirety). The externalization of PE and the local enrichment of PS in the inner surface of MPs were correlated with an elevated presence of small GTPases in a polybasic region (PBR)-dependent fashion (Hou et al. *J Extracell Vesicles.* 2014, 3; herein incorporated by reference in its entirety). Accumulating evidence indicated that the redistribution of aminophospholipids may play a role in mediating membrane reorganization. In the budding yeast, the local enrichment of PS at the inner membrane leaflet is essential for the maintenance of cell polarity (Fairn et al. *Nat*

Cell Biol. 2011, 13, 1424-1430; Das et al. *Nat Cell Biol.* 2012, 14, 304-310; herein incorporated by reference in their entireties). It is contemplated that a greater anionic density electrostatically attracts cationic membrane-interacting proteins, such as the small GTPases, in a polybasic region (PBR)-dependent fashion. The enrichment of PS at the inner leaflet is accompanied by the transbilayer movement of PE to the outer leaflet. In mammalian cells, local enrichment of PS/PIs at the inner leaflet of the plasma membrane is associated with the recruitment of RhoA at the cleavage furrow during cytokinesis, where PE externalization is essential for the completion of cell division (K. Emoto, H. Inadome, Y. Kanaho, S. Narumiya, M. Umeda. *J Biol Chem.* 2005, 280, 37901-37907; herein incorporated by reference in its entirety). TAT-5, which is a PE-specific P4 ATPase in C. elegans, suppresses the budding of extracellular vesicles presumably by preventing the externalization of PE (Wehman, C. Poggioli, P. Schweinsberg, B. D. Grant, J. Nance. *Curr Biol.* 2011, 21, 1951-1959; herein incorporated by reference in its entirety). Experiments conducted during development of embodiments described herein demonstrated probe utility for staining cancer cell-derived MPs in a single step (FIGS. 13D and E). By substituting the 2-step staining technique (biotinlyated duramycin followed by avidin-FITC), the current technique is more convenient and minimizes risk for toxicity-induced artifacts.

Figure 14:
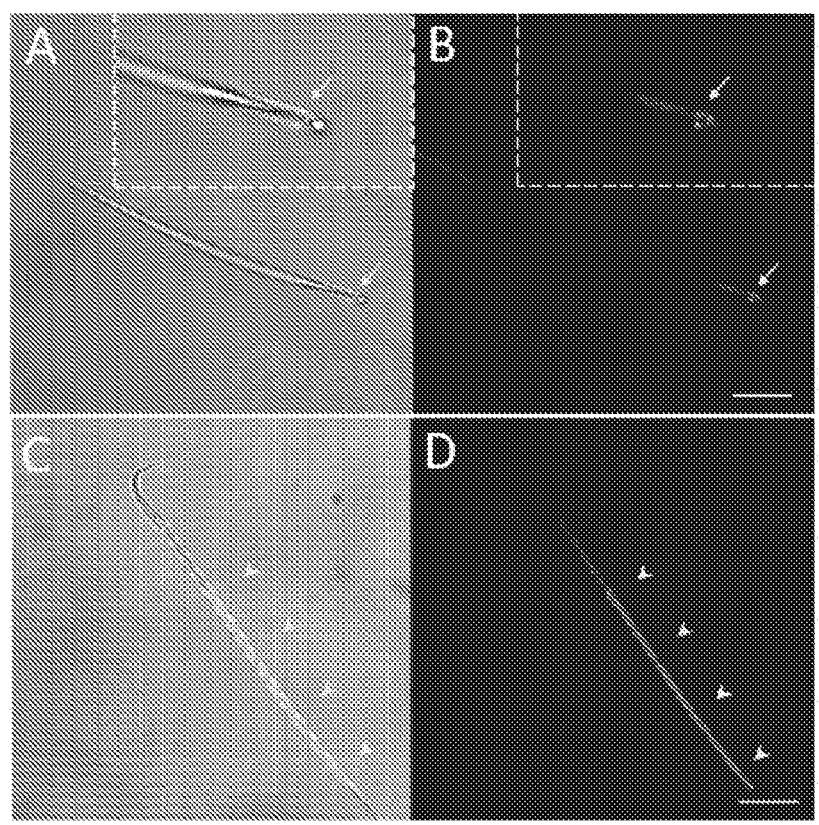
FIG. 14A-D shows staining studies on sperm cells. (A-B) The presence of PE at the apical region (arrows) of a rat sperm cell after capacitation, as detected in phase contrast and confocal micrographs. A magnified view is shown in insets. (C-D) Duramycin-GFP positive staining of the upper segment of rat sperm flagellum (arrow heads). Scale bar=10 µm.

The capacitation of sperm cells is necessary for fertilization of the egg. During this process, the phospholipid membrane at the apical area of sperm head becomes more fluidic, and is accompanied with the translocation of PE and PS to the outer leaflet (Gadella & Harrison. *Biol Reprod.* 2002, 67, 340-350; herein incorporated by reference in its entirety). It is contemplated that the phospholipid flip-flop is mediated by a scramblase in a protein kinase A-dependent fashion, and is independent of the apoptotic pathway. The externalization of these phospholipids, particularly PE, is thought to facilitate membrane fusion and the subsequent fertilization of the egg. In the current study, using duramycin-GFP as a probe, the presence of PE at the outer surface of sperm apical membrane after capacitation was demonstrated (FIGS. 14A and B), which is consistent with the prior observation accomplished using a complex consisting biotinylated cinnamycin and FITC-conjugated streptavidin. The current probe thus provides a means to characterize the kinetics of membrane reorganization in reproductive biology. Additionally, a portion of rat sperms treated under the current condition were stained positive for duramycin-GFP at the tail region, possibly the upper segment of the flagellum, whereas the acrosome, mid-piece and the end-piece remained negative. An example of this staining pattern is shown in FIGS. 14C and D. The sperms stained positive for duramycin-GFP in this fashion were negative for propidium iodide, indicating that this staining pattern was a result of PE externalization without compromised membrane integrity.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by number or author last name, are herein incorporated by reference in their entireties.

[1] G. van Meer, D. R. Voelker, G. W. Feigenson. *Nat Rev Mol Cell Biol.* 2008, 9, 112-124.

[2] T. G. Kutateladze. *Nat Chem Biol.* 2010, 6, 507-513.

[3] S. Jean, A. A. Kiger. *Nat Rev Mol Cell Biol.* 2012, 13, 463-470.

[4] J. G. Kay, S. Grinstein. *Adv Exp Med Biol.* 2013, 991, 177-193.

[5] T. Yeung, G. E. Gilbert, J. Shi, J. Silvius, A. Kapus, S. Grinstein. *Science.* 2008, 319, 210-213.

[6] J. E. Vance, G. Tasseva. *Biochim Biophys Acta.* 2013, 1831, 543-554.

[7] S. Wang, S. Zhang, L. C. Liou, Q. Ren, Z. Zhang, G. A. Caldwell, K. A. Caldwell, S. N. Witt. *Proc Natl Acad Sci U.S.A.* 2014, 111, Epub.

[8] T. Tatsuta, M. Scharwey, T. Langer. *Trends Cell Biol.* 2014, 24, 44-52.

[9] T. T. Sebastian, R. D. Baldridge, P. Xu, T. R. Graham. *Biochim Biophys Acta.* 2012, 1821, 1068-1077.

[10] M. Bogdanov, W. Dowhan, H. Vitrac. *Biochim Biophys Acta.* 2014, 1843, 1475-1488.

[11] A. K. Menon, V. L. Stevens. *J Biol Chem.* 1992, 267, 15277-15280.

[12] T. Hanada, Y. Satomi, T. Takao, Y. Ohsumi. *FEBS Lett.* 2009, 583, 1078-83.

[13] L. Yang, L. Ding, H. W. Huang. *Biochemistry.* 2003, 42, 6631-6635.

[14] D. P. Siegel, R. M. Epand. *Biochim Biophys Acta.* 2000, 1468, 87-98.

[15] J. Navarro, J. Chabot, K. Sherrill, R. Aneja, S. A. Zahler, E. Racker. *Biochemistry.* 1985 Aug. 13; 24(17): 4645-50.

[16] G. Machaidze, J. Seelig. *Biochemistry.* 2003, 42, 12570-12576.

[17] G. Machaidze, A. Ziegler, J. Seelig. *Biochemistry.* 2002, 41, 1965-1971.

[18] Y. Aoki, T. Uenaka, J. Aoki, M. Umeda, K. Inoue. *J Biochem.* 1994, 116, 291-297.

[19] M. Zhao. *Amino Acids.* 2011, 41, 1071-1079.

[20] M. Zhao, Z. Li, S. Bugenhagen. *J Nucl Med.* 2008, 49, 1345-1352.

[21] A. Makino, T. Baba, K. Fujimoto, K. Iwamoto, Y. Yano, N. Terada, S. Ohno, S. B. Sato, A. Ohta, M. Umeda, K. Matsuzaki, T. Kobayashi. *J Biol Chem.* 2003, 278, 3204-3209.

[22] S. J. Martin, C. P. Reutelingsperger, A. J. McGahon, J. A. Rader, R. C. van Schie, D. M. LaFace, D. R. Green. *J Exp Med.* 1995, 182, 1545-1556.

[23] K. Emoto, N. Toyama-Sorimachi, H. Karasuyama, K. Inoue, M. Umeda. *Exp Cell Res.* 1997, 232, 430-434.

[24] A. Shiratsuchi, S. Osada, S. Kanazawa, Y. Nakanishi. *Biochem Biophys Res Commun.* 1998, 246, 549-555.

[25] V. Muralidharan-Chari, J. W. Clancy, A. Sedgwick, C. D'Souza-Schorey. *J Cell Sci.* 2010, 123, 1603-1611.

[26] S. Hou, D. Grillo, C. L. Williams, J. A. Wasserstrom, I. Szleifer, M. Zhao. *J Extracell Vesicles.* 2014, 3.

[27] G. D. Fairn, M. Hermansson, P. Somerharju, S. Grinstein. *Nat Cell Biol.* 2011, 13, 1424-1430.

[28] A. Das, B. D. Slaughter, J. R. Unruh, W. D. Bradford, R. Alexander, B. Rubinstein, R. Li. *Nat Cell Biol.* 2012, 14, 304-310.

[29] K. Emoto, H. Inadome, Y. Kanaho, S. Narumiya, M. Umeda. *J Biol Chem.* 2005, 280, 37901-37907.

[30] A. M. Wehman, C. Poggioli, P. Schweinsberg, B. D. Grant, J. Nance. *Curr Biol.* 2011, 21, 1951-1959.

[31] B. M. Gadella, R. A. Harrison. *Biol Reprod.* 2002, 67, 340-350.

The invention claimed is:

1. A composition comprising a conjugate of duramycin, a fluorescent protein and a nuclear localization signal, wherein the fluorescent protein is chemically or enzymatically tethered to a PEG or peptide linker which is also chemically or enzymatically tethered to the N-terminus of duramycin, or alternatively, the fluorescent protein and duramycin conjugate is a single protein unit produced recombinantly.

2. The composition of claim 1, wherein the nuclear localization signal is Tat peptide.

* * * * *

SEQUENCE LISTING

<160> NUMBER OF SEQ ID NOS: 3

<210> SEQ ID NO 1
<211> LENGTH: 19
<212> TYPE: PRT
<213> ORGANISM: Artificial sequence
<220> FEATURE:
<223> OTHER INFORMATION: Synthetic

<400> SEQUENCE: 1

Cys Ala Asn Ser Cys Ser Tyr Gly Pro Leu Thr Trp Ser Cys Asp Gly
1               5                   10                  15

Asn Thr Lys

<210> SEQ ID NO 2
<211> LENGTH: 51
<212> TYPE: DNA
<213> ORGANISM: Artificial sequence
<220> FEATURE:
<223> OTHER INFORMATION: Synthetic

<400> SEQUENCE: 2
cttggctacg gccgccagca aggcggccag ggcggccgcg gtggatccac c          51

<210> SEQ ID NO 3
<211> LENGTH: 51
<212> TYPE: DNA
<213> ORGANISM: Artificial sequence
<220> FEATURE:
<223> OTHER INFORMATION: Synthetic

<400> SEQUENCE: 3
ggtggatcca ccgcggccgc cctggccgcc ttgctggcgg ccgtagccaa g          51